(12) United States Patent
Elia

(10) Patent No.: US 11,077,029 B2
(45) Date of Patent: Aug. 3, 2021

(54) INTERACTIVE NGT SYSTEM

(71) Applicant: ART MEDICAL Ltd., Netanya (IL)

(72) Inventor: Liron Elia, Kiryat-Ata (IL)

(73) Assignee: ART MEDICAL Ltd., Netanya (IL)

(*) Notice: Subject to any disclaimer, the term of this patent is extended or adjusted under 35 U.S.C. 154(b) by 0 days.

(21) Appl. No.: 16/383,837

(22) Filed: Apr. 15, 2019

(65) Prior Publication Data

US 2019/0240115 A1 Aug. 8, 2019

Related U.S. Application Data

(63) Continuation of application No. 15/477,194, filed on Apr. 3, 2017, now Pat. No. 10,258,542, which is a
(Continued)

(51) Int. Cl.
*A61J 15/00* (2006.01)
*A61M 1/00* (2006.01)
(Continued)

(52) U.S. Cl.
CPC ............. *A61J 15/00* (2013.01); *A61B 5/0084* (2013.01); *A61B 5/01* (2013.01); *A61B 5/037* (2013.01); *A61B 5/0538* (2013.01); *A61B 5/14539* (2013.01); *A61B 5/4233* (2013.01); *A61B 5/4238* (2013.01); *A61B 5/4836* (2013.01); *A61J 15/0003* (2013.01); *A61J 15/008* (2015.05); *A61J 15/0073* (2013.01); *A61J 15/0076* (2015.05); *A61J 15/0084* (2015.05);
(Continued)

(58) Field of Classification Search
CPC ...... A61J 15/00; A61J 15/0076; A61J 15/008; A61J 15/0084; A61J 15/0088; A61M 1/0025; A61B 5/0084; A61B 5/01; A61B 5/037; A61B 5/0538; A61B 5/14539
USPC .......................................................... 604/513
See application file for complete search history.

(56) References Cited

U.S. PATENT DOCUMENTS 3,734,094 A 5/1973 Calinog
4,828,550 A 5/1989 Kurimoto
(Continued)

FOREIGN PATENT DOCUMENTS

WO WO 92/17150 10/1992
WO WO 01/87138 11/2001
(Continued)

OTHER PUBLICATIONS

Advisory Action Before the Filing of an Appeal Brief dated Nov. 10, 2015 From the U.S. Patent and Trademark Office Re. U.S. Appl. No. 12/529,549.
(Continued)

*Primary Examiner* — Phillip A Gray

(57) ABSTRACT

Disclosed is an NGT system, the system comprises a nasogastric tube having a diameter and length configured to pass through an esophagus such that the lumen of the NGT maintains fluid communication with a portion of the digestive tract, and a digestive tract sensor operatively associated with the NGT, the digestive tract sensor configured to sense from inside the body and transmit signals in response to one or both of conditions relating to nourishment states of the digestive tract, and positioning of the NGT.

23 Claims, 14 Drawing Sheets

Related U.S. Application Data continuation of application No. 15/081,895, filed on Mar. 27, 2016, now Pat. No. 9,610,227, which is a continuation of application No. 12/529,549, filed as application No. PCT/IL2008/000265 on Mar. 2, 2008, now Pat. No. 9,295,395.

(60) Provisional application No. 60/904,326, filed on Mar. 2, 2007.

(51) Int. Cl.

| | | |
|---|---|---|
| *A61B 5/145* | (2006.01) | |
| *A61B 5/00* | (2006.01) | |
| *A61B 5/03* | (2006.01) | |
| *A61B 5/01* | (2006.01) | |
| *A61B 5/0538* | (2021.01) | |

(52) U.S. Cl.
CPC ........ *A61J 15/0088* (2015.05); *A61M 1/0025* (2014.02); *A61M 1/0066* (2013.01); *A61B 5/145* (2013.01); *A61M 2205/3317* (2013.01); *A61M 2205/3324* (2013.01); *A61M 2205/3344* (2013.01); *A61M 2205/3368* (2013.01); *A61M 2210/1053* (2013.01)

(56) References Cited

U.S. PATENT DOCUMENTS

| | | | |
|---|---|---|---|
| 4,921,481 A | 5/1990 | Danis et al. | |
| 5,065,754 A | 11/1991 | Jensen | |
| 5,334,167 A | 8/1994 | Cocanower | |
| 5,411,022 A | 5/1995 | McCue et al. | |
| 5,417,664 A | 5/1995 | Felix et al. | |
| 5,833,625 A | 11/1998 | Essen-Moller | |
| 6,334,064 B1 * | 12/2001 | Fiddian-Green ... | A61B 5/14539 600/311 |
| 6,935,339 B2 | 8/2005 | Mattar Neto et al. | |
| 2006/0259010 A1 | 11/2006 | Stefanchik et al. | |
| 2008/0167607 A1 | 7/2008 | Pfeiffer et al. | |
| 2016/0206517 A1 | 7/2016 | Elia | |
| 2017/0202750 A1 | 7/2017 | Elia | |

FOREIGN PATENT DOCUMENTS

| | | |
|---|---|---|
| WO | WO 2002/32477 | 4/2002 |
| WO | WO 2005/104989 | 11/2005 |
| WO | WO 2008/107872 | 9/2008 |

OTHER PUBLICATIONS

Advisory Action Before the Filing of an Appeal Brief dated Oct. 31, 2013 From the U.S. Patent and Trademark Office Re. U.S. Appl. No. 12/529,549.
Applicant-Initiated Interview Summary dated Sep. 13, 2018 From the U.S. Patent and Trademark Office Re. U.S. Appl. No. 15/477,194. (4 pages).
International Preliminary Report on Patentability dated Oct. 22, 2009 From the International Bureau of WIPO Re.: Application No. PCT/IL2008/000265.
International Search Report and the Written Opinion dated Jul. 22, 2008 From the International Searching Authority Re.: Application No. PCT/IL2008/000265.
Official Action dated Dec. 3, 2012 From the U.S. Patent and Trademark Office Re. U.S. Appl. No. 12/529,549.
Official Action dated Jul. 15, 2015 From the U.S. Patent and Trademark Office Re. U.S. Appl. No. 12/529,549.
Official Action dated Dec. 16, 2014 From the U.S. Patent and Trademark Office Re. U.S. Appl. No. 12/529,549.
Official Action dated Jun. 29, 2018 From the U.S. Patent and Trademark Office Re. U.S. Appl. No. 15/477,194. (10 pages).
Official Action dated Jul. 30, 2013 From the U.S. Patent and Trademark Office Re. U.S. Appl. No. 12/529,549.
Official Action dated Jun. 30, 2016 From the U.S. Patent and Trademark Office Re. U.S. Appl. No. 15/081,895.
Supplementary European Search Report and the European Search Opinion dated Apr. 10, 2013 From the European Patent Office Re. Application No. 08719899.0.

\* cited by examiner

INTERACTIVE NGT SYSTEM

RELATED APPLICATIONS

This application is a continuation of U.S. patent application Ser. No. 15/477,194, filed on Apr. 3, 2017, which is a continuation of U.S. patent application Ser. No. 15/081,895, filed on Mar. 27, 2016, now U.S. Pat. No. 9,610,227, which is a continuation of U.S. patent application Ser. No. 12/529,549 filed on Sep. 2, 2009, now U.S. Pat. No. 9,295,395, which is a National Phase Application of PCT Patent Application No. PCT/IL2008/000265 having International Filing Date of Mar. 2, 2008, which claims the benefit of priority of US Provisional Patent Application No. 60/904,326, filed on Mar. 2, 2007. The contents of the above applications are all incorporated by reference as if fully set forth herein in their entirety.

FIELD AND BACKGROUND OF THE INVENTION

The present invention, in some embodiments thereof, relates to an interactive nasogastric tube (NGT) system.

A NGT provides direct transfer of food and/or an active pharmaceutical agent (API) to the stomach; both food and API being alternatively referred to herein using the general term "nourishment".

To provide a supply of nourishment, the nourishment is typically placed in a reservoir that is higher than the patient's stomach and passes into the stomach through the NGT under the influence of gravity.

In intermittent and/or supervised nourishment, the NGT is connected to a reservoir containing the nourishment and an electronic pump controls and/or measures dispensation.

An NGT, though providing life-giving nourishment, does not prevent aspiration in which gastric contents, including gastric acids and undigested food enter the lungs. The lungs aspirate the gastric contents during inspiration of air, resulting in devastating consequences, for example aspiration pneumonia and/or death.

The prevalence of aspiration pneumonia is estimated to be as high as 95% of NGT nourished patients, and the mortality rate is estimated to be as high as 62%. *American gastroenterological association technical review on tube feeding for enteral nutrition. Gastroenterology* 1995; 108:3-21.

Methods for detecting aspiration of gastric contents include colored nourishment and pH monitoring. In colored nourishment, green or blue food coloring is added to the nourishment entering the stomach via the NGT tube. The presence of food coloring in the mouth indicates that gastric contents have been expelled from the stomach and are being aspirated by the lungs.

In pH monitoring, a pH sensor in the lungs sets off a signal when the normal lung pH of 7.6 drops due to the presence of gastric fluid in the lungs which have a typical pH of less than 4. The accuracy of detecting aspiration with a pH sensor, however, may be significantly compromised in the presence of H2 blockers and/or antacids that typically raise gastric fluid pH.

In typical NGT systems, the NGT may be improperly positioned, herein malpositioned, during or following NGT placement; a common occurrence in patients having impaired consciousness and in infants. To confirm proper NGT positioning, a radiograph interpreted by a radiologist may be required several times a day for a single patient with impaired consciousness on NGT nourishment; while radiographic confirmation may be required as often as 12 times per day for an infant.

The frequency of radiographs makes it impractical, if not impossible, to request radiographic assessment of NGT position by the radiologist. Without the input of a radiologist, a malpositioned NGT may be misdiagnosed by the nurse as being properly positioned, resulting in danger of aspiration to the infant.

Patents to devices designed to prevent NGT aspiration include:

U.S. Pat. No. 3,734,094 which teaches an NGT including a heart and lung acoustic monitor;

U.S. Pat. No. 5,065,754 teaches an NGT including a ventilator having lung pressure sensors;

U.S. Pat. No. 6,935,339 teaches an NGT including a secretion suctioning device; and U.S. Pat. No. 5,417,664 teaches an NGT including a filter to stop some movement of reflux.

SUMMARY OF THE INVENTION

The present invention, in some embodiments thereof, relates to an interactive NGT system that interacts with the digestive tract to apprise an operator of one or more states of the digestive tract and provide safe NGT nourishment to a patient. The interactive NGT system is optionally provided on a single lumen NGT, or alternatively, on a double lumen NGT. Optionally, the interactive NGT system provides nourishment from multiple nourishment sources, for example from a food container, an antacid container and a vitamin container.

In embodiments, the interactive NGT system comprises one or more sleeves that add onto an existing NGT.

In some embodiments, the NGT is not interactive, for example, serving to prevent dripping.

According to an aspect of the some embodiments of the invention, there is provided an NGT system, comprising a nasogastric tube having a diameter and length configured to pass through an esophagus such that the lumen of the NGT maintains fluid communication with a portion of the digestive tract, and a digestive tract sensor operatively associated with the NGT, the digestive tract sensor configured to sense from inside the body and transmit signals in response to one or both of conditions relating to nourishment states of the digestive tract, and positioning of the NGT.

According to some embodiments of the inventions, the sensor includes at least one of a light emitting source, a pH sensor, an electromagnetic source, a thermocouple, and a pressure sensor.

According to some embodiments of the inventions, the system includes a controller in communication with the digestive tract sensor the controller including at least one audiovisual display configured to provide an audiovisual output in response to the transmitted signals.

According to some embodiments of the inventions, the system includes a nourishment pump operatively associated with the controller and connected to the lumen of the NGT, wherein the controller is configured to control the movement of nourishment through the nourishment pump in response to signals received by the controller from the digestive tract sensor.

According to some embodiments of the inventions, the NGT has a diameter configured for insertion through an infant esophagus.

According to some embodiments of the inventions, the NGT comprises more than two lumens in at least one configuration of side-by-side, and axially.

According to some embodiments of the inventions, the sensor comprises at least one gastric fluid sensor and the audiovisual display is configured to provide output signaling proper positioning of the NGT.

According to some embodiments of the inventions, the gastric fluid sensor is configured to distinguish between saliva and gastric fluids.

According to some embodiments of the inventions, the at least one gastric fluid sensor is additionally configured to sense gastric reflux and the audiovisual display is configured to provide output signaling the presence of reflux.

According to some embodiments of the inventions, the at least one gastric fluid sensor is positioned in at least one position along the NGT, the position comprising at the end of the NGT, and along a mid portion of the NGT that is in contact with the esophagus.

According to some embodiments of the inventions, the fluid gastric sensor at the end of the NGT positioned to sense gastric fluid in at least one of forward of the NGT, and to the sides of the NGT.

According to some embodiments of the inventions, the gastric reflux sensor is configured to distinguish between saliva and gastric fluids.

According to some embodiments of the inventions, the system includes a suction pump operatively associated with the controller and connected to the lumen of the NGT, wherein the controller is configured to control the suction of reflux through the NGT in response to signals received by the controller from the digestive tract sensor.

According to some embodiments of the inventions, the sensor comprises at least one nourishment fluid sensor and the audiovisual display is configured to provide output signaling proper nourishment.

According to some embodiments of the inventions, the nourishment sensor senses at least one of food nourishment, and API nourishment.

According to some embodiments of the inventions, the system includes a sleeve having a lumen comprising an inside diameter sufficient to slidingly pass over the nasogastric tube.

According to some embodiments of the inventions, the system includes at least one spacer configured to maintain a space between the NGT and the sleeve.

According to some embodiments of the inventions, the at least one spacer comprises at least one of a spacer projecting radially inwardly into the lumen of the sleeve, and a spacer projecting radially outward from the NGT.

According to some embodiments of the inventions, the sleeve is positionally adjustable along the NGT.

According to another aspect of the some embodiments of the invention, there is provided a NGT system, comprising a suction sleeve comprising a lumen and a diameter configured to pass through an esophagus, an NGT having an outside diameter configured to slidingly pass through the lumen of the suction sleeve, and at least one spacer located between the suction sleeve and the NGT, the spacer configured to separate at least a portion of the surfaces of the sleeve and the NGT.

According to some embodiments of the inventions, the system includes at least one spacer configured to maintain a space between the suction sleeve and the NGT.

According to some embodiments of the inventions, wherein the at least one spacer comprises at least one of a spacer projecting radially inwardly into the lumen of the suction sleeve, and a spacer projecting radially outward from the NGT.

According to some embodiments of the inventions, the system includes a digestive tract sensor operatively associated with the NGT, the digestive tract sensor configured to sense conditions in the digestive tract and transmit audiovisual signals in response to the conditions.

According to some embodiments of the inventions, the system includes a pump controller in communication with the digestive tract sensor, and an NGT pump operatively associated with the controller and connected to the lumen of the NGT, the controller configured control pumping of the pump in response to signals received by the controller from the digestive tract sensor.

According to some embodiments of the inventions, the NGT pump provides at least one of positive pressure, and negative pressure.

According to some embodiments of the inventions, the pump provides at least one of nourishment to the digestive tract, and evacuation of fluids from the digestive tract.

According to some embodiments of the inventions, the system includes a gastric sensor operatively associated with the suction sleeve and connected to the controller, the sensor configured to sense and transmit signals in response to conditions in the digestive tract, and a suction sleeve pump operatively associated with the controller and connected to the lumen of the suction sleeve, the controller configured control pumping of the pump in response to sensor signals received by the controller from the digestive tract sensor.

According to some embodiments of the inventions, the suction sleeve pump provides at least one of positive pressure, and negative pressure.

According to some embodiments of the inventions, the sensor senses at least one of a gastric reflux sensor, a suction sleeve positioning sensor, and a nourishment sensor.

According to some embodiments of the inventions, the nourishment sensor senses at least one of food nourishment, and API nourishment.

According to some embodiments of the inventions, the gastric reflux sensor comprises at least one of a gastric content sensor located at the end of the suction sleeve, and a reflux sensor located a distance from the end of the suction sleeve.

According to some embodiments of the inventions, the gastric reflux sensor is configured to distinguish between saliva and gastric fluids.

According to some embodiments of the inventions, the system includes multiple sensors and multiple audiovisual displays, each audiovisual display in communication with at least one sensor.

According to some embodiments of the inventions, the sensor includes at least one of a light emitting source, a pH sensor, an electromagnetic source, a thermocouple, and a pressure sensor.

According to still another aspect of the some embodiments of the invention, there is provided a method for positioning a tube in the digestive tract, the method comprising locating a sensor located on a tube, pushing the tube through a portion of the digestive tract, receiving operator-interpretable sensor signals from inside the body including at least one of that the sensor is inside stomach, proximate to an esophageal sphincter, within an esophageal sphincter, and refining the position of the tube based upon the operator-interpretable sensor signals.

According to some embodiments of the inventions, the method includes at least one of inserting the tube through the patient mouth, and inserting the tube through the patient naso-pharynx.

According to some embodiments of the inventions, the tube has a diameter and length configured to pass through the esophagus of an infant.

According to still further aspects of the some embodiments of the invention, there is provided a method for dispensing nourishment via a tube, the method comprising locating a sensor located on a tube, pushing the tube through a portion of the digestive tract, receiving operator-interpretable sensor signals from inside the body that the tube is inside stomach, and dispensing nourishment to the stomach via the tube.

According to some embodiments of the inventions, the method includes at least one of inserting the tube through the patient mouth, and inserting the tube through the patient naso-pharynx.

According to some embodiments of the inventions, the tube has a diameter and length configured to pass through the esophagus of an infant.

According to some embodiments of the inventions, the method includes protecting the esophagus from contact with gastric fluid while removing the tube.

According to an additional aspect of the some embodiments of the invention, there is provided an NGT system, comprising a suction sleeve comprising a lumen and a diameter configured to pass through an esophagus, an NGT lumen surrounded by the suction sleeve, and at least one suction source connected to the suction sleeve.

According to some embodiments of the inventions, the NGT lumen is provided in a tube slidingly received by the suction sleeve.

According to some embodiments of the inventions, the NGT lumen is integral to the suction sleeve.

According to still another aspect of the some embodiments of the invention, there is provided a method for isolating a gastric tube from the esophagus, the method comprising enclosing at least an end of a gastric tube inside a sleeve after the gastric tube is inserted into the stomach, and retracting the gastric tube out of an esophagus following the enclosing.

According to some embodiments of the inventions, the method includes retracting the sleeve simultaneously with the gastric tube.

According to still another aspect of the some embodiments of the invention, there is provided a method for providing nourishment to a patient, the method comprising providing a nourishment plan for a given patient, applying the nourishment plan via an NGT tube, and stopping and/or continuing the applying in response to a sensor measurement in according with the nourishment plan.

According to some embodiments of the inventions, the sensor measures reflux and then continues with nourishment plan.

According to some embodiments of the inventions, the sensor measures emptiness of stomach and then continues with nourishment plan.

According to some embodiments of the inventions, the nourishment plan comprises both drug and food.

According to some embodiments of the inventions, the nourishment plan comprises is at least one of a multimeal plan, and a multiday plan.

According to still another aspect of the some embodiments of the invention, there is provided a method of controlling feeding via a gastric tube into a stomach, the method comprising causing a pressure inside a gastric tube, measuring a pressure associated with the gastric tube, and changing the pressure in response to the measurement.

According to some embodiments of the inventions, the pressure comprises a positive pressure.

According to some embodiments of the inventions, the positive pressure is applied to a food.

According to some embodiments of the inventions, the pressure comprises a negative pressure.

According to some embodiments of the inventions, the negative pressure is applied to a gastric fluid.

According to still another aspect of the some embodiments of the invention, there is provided a method of controlling feeding via a gastric tube into a stomach, the method comprising measuring, using a sensor on a gastric tube, changing a nourishment parameter in response to the measurement.

According to still another aspect of the some embodiments of the invention, there is provided a sleeve for an NGT tube, comprising a body having an outer diameter suitable for passing through an esophagus and a lumen having an inner diameter suitable for receiving an NGT tube therethrough, and a sensor mounted on a distal side of the body.

According to still another aspect of the some embodiments of the invention, there is provided an NGT system comprising an inner NGT, and an outer sleeve snugly and slidably mounted on the inner NGT.

According to still another aspect of the some embodiments of the invention, there is provided an NGT console system, comprising an input for receiving a sensor reading, a controller configured fro receiving the sensor reading and generating an alert signal in response thereto, and an actuator for at least one of a suction pump, and a nourishment pump.

According to some embodiments of the inventions, the alert signal automatically controls the actuator.

According to some embodiments of the inventions, the alert signal comprises an audiovisual output.

According to some embodiments of the inventions, the actuator is configured for mounting on standard on standard nasogastric feeding system.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, software, firmware or a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1a and 1c are schematic views of an interactive NGT system inserted into a patient, according to some embodiments of the invention;

FIG. 1b is a flow chart of the operation of the interactive NGT system of FIG. 1a, according to some embodiments of the invention;

FIG. 2 is a schematic view of portions of the interactive NGT system of FIG. 1a, according to some embodiments of the invention;

FIG. 3 is a schematic view of a gastric console and interactive NGT system of FIG. 1a, according to some embodiments of the invention;

FIGS. 4-6, 7a-7b and 8 are details of different configurations of the interactive NGT system of FIG. 1a and portions thereof, according to some embodiments of the invention;

FIGS. 9a-9b, 10 and 11a-11b are details of alternative sensors associated with a portion of the interactive NGT system of FIG. 1a, according to some embodiments of the invention; and FIG. 12 is a detailed schematic view of the gastric console and interactive NGT system shown in FIG. 3, according to some embodiments of the invention.

DESCRIPTION OF SPECIFIC EMBODIMENTS OF THE INVENTION

Interactive NGT System

Figure 1A:
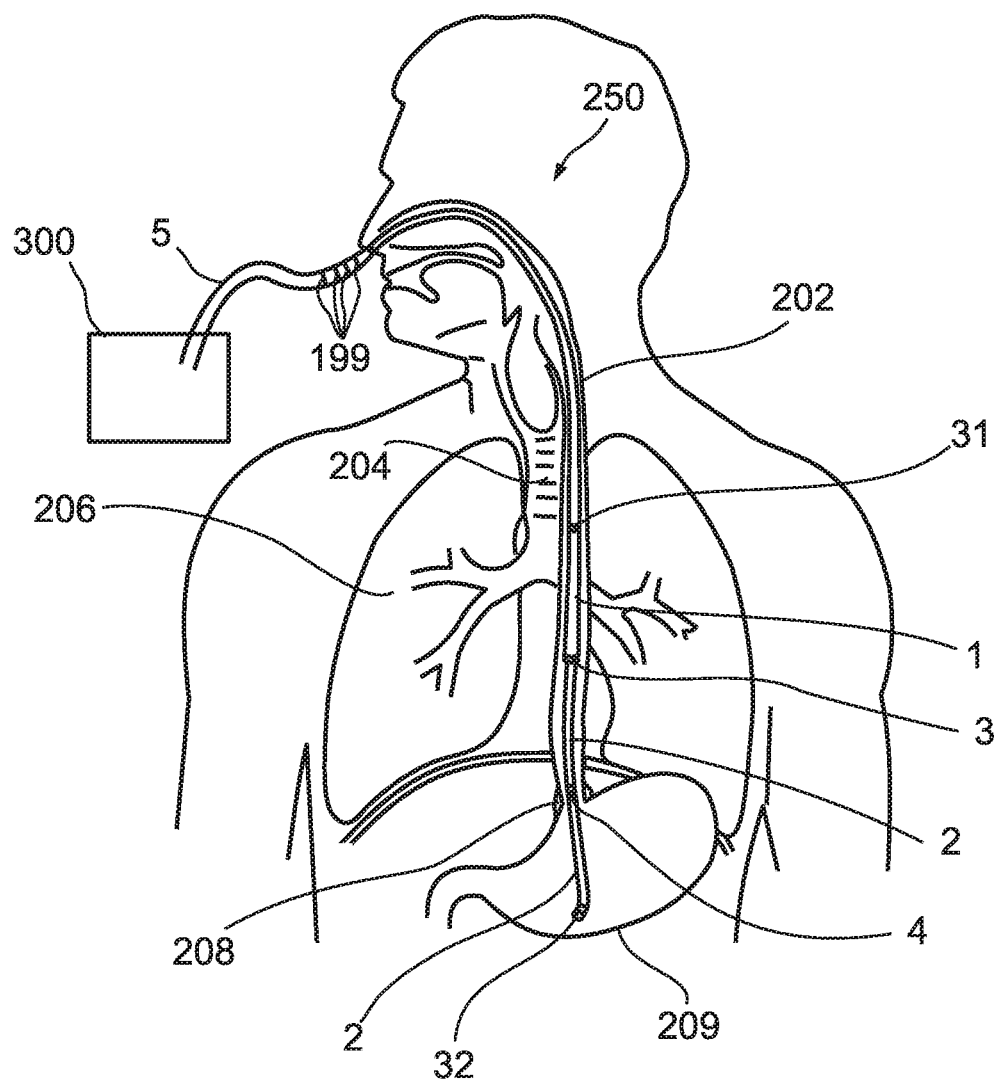

The present invention, in some embodiments thereof, relates to an interactive NGT system that interacts with the digestive tract to apprise an operator of one or more states of the digestive tract and provide safe NGT nourishment to a patient. The interactive NGT system is optionally provided on a single lumen NGT, or alternatively, on a double lumen NGT. Optionally, the interactive NGT system provides nourishment from multiple nourishment sources, for example from a food container, an antacid container and a vitamin container.

In embodiments, the interactive NGT system comprises one or more sleeves that add onto an existing NGT. In some embodiments, the NGT is not interactive, for example, serving to prevent dripping.

Initially, single lumen NGT embodiments of the interactive NGT system will be presented; though it should be understood that the single lumen NGT embodiments are configurable for use with the double lumen NGT embodiments.

Digestive Tract Sensors

In some embodiments the interactive NGT system includes sensors that sense, inter alia, the state of various portions of the digestive tract; for example, food level, reflux state and/or position of an NGT system in the digestive tract.

In some embodiments, the interactive digestive system includes a console that provides audiovisual signals to assist an operator in performing one or more of a variety of digestive tract-related tasks.

Optionally, the console includes a controller and positive and/or negative pressure pumps and/or automatically controls providing nourishment and/or suction of caustic substances in response to signals from the sensor.

Positioning Sensor

In embodiments, the interactive NGT system provides guidance to an operator in positioning the NGT in the stomach.

For example, a positioning sensor provides signals that the NGT is near the esophageal sphincter, is passing the esophageal sphincter and/or is in the stomach; and the console interprets the signals and provides audiovisual output to an operator and/or automated actions. It should be noted that in some embodiments a single sensor can have multiple functions, for example, positioning and detecting reflux as will be explained below.

NGT Positioning

There are multiple methods and sensor configurations, provided by various embodiments of the invention, by which the operator can ensure proper positioning of the NGT within the stomach.

In one method, a sensor is located at the tip of the NGT and the operator pushes the NGT through the esophagus until receiving signals from the console that the tip is at the esophageal sphincter. The operator then pushes the NGT, for example, approximately 5-10 centimeters, so that the tip (or feeding exits of the tube) is positioned in the gastric cavity.

In another embodiment, the sensor is located about 10 centimeters from the NGT tip. When the consol notifies the operator that the sensor is positioned within gastric fluid and/or at or past the sphincter (depending on sensor type), the operator pulls the NGT retrograde about 5 centimeters to achieve proper positioning of the tip within the stomach.

Following positioning, the positioning sensor optionally monitors the position of the end of the NGT optionally using a gastric fluid sensor. Should the NGT become malpositioned, the sensor loses contact with the gastric fluid and the sensor sends a signal (or a continuously sent signal changes in a manner that exceeds some range, and then the console optionally provides an audiovisual display that alerts the operator that the NGT is improperly positioned. In an alternative embodiment, the sensor continuously sends signals and a change in a manner that exceeds a predefined range alerts operator that the NGT is improperly positioned.

In some embodiments, the console provides multiple signals of increasing magnitude to indicate increasing urgency. The operator then manipulates the NGT until the console signals that the NGT is properly placed. In some embodiments automatic action is provided by the console, including, inter alia, tube movement, feeding stopping, and/or suction application.

Interactive NGT

In some embodiments, the controller is connected to a nourishment dispensing assembly, including a nourishment pump, and the operator uses appropriate controls, such as buttons on the console, to begin dispensing nourishment.

In some embodiments, a patient nourishment schedule geared to, inter alia, the weight and/or nourishment needs of the patient being treated, is optionally contained within the controller and the controller provides nourishment according to the patient nourishment schedule, optionally taking into account manual and/or automated feed stoppages due to reflux and/or other feeding problems.

Aspiration Protection

In some embodiments, the NGT provides additional safety against gastric reflux. In some embodiments, a reflux sensor, separate from the gastric sensor, senses the presence of gastric reflux in the stomach. In other embodiments, the same sensor that senses the presence of gastric fluid is configured to additionally sense gastric reflux.

During nourishment, gastric acids mix with the nourishment, thereby raising the pH of the gastric fluid. Prior to reflux, low pH gastric fluids accumulate in the stomach, thereby lowering the gastric fluid pH.

When the gastric fluid pH drops below a specific level of acidity the gastric fluid sensor optionally senses the drop in pH. The console signals the operator that low pH gastric acid is building up in the stomach and that it may soon be expelled and aspirated.

To stop increasing pressure in the stomach that increases the chances of reflux, the operator, as prompted by the console (or with the console performing automatic functions), immediately stops the nourishment pump and/or removes the NGT. The operator resumes providing nourishment when the console signals an appropriate rise in pH.

Optionally, the nourishment pump does not resume pumping until the operator manually resets the nourishment pump and initiates its operation.

In some embodiments, the console provides audiovisual output to the operator requesting that the NGT be removed until the danger of aspiration passes. By removing the NGT, the effective size of the esophageal lumen is increased; reducing pressure of reflux that may have entered the esophagus, thereby reducing the chances that reflux will be expelled and aspirated.

Single lumen interactive NGTs having a larger outside diameter may be used in human teenagers and adults. The interactive NGT may be additionally adapted for use in animals by modifying the length and/or diameter of the NGT system. Optionally, the system is used for infants, for example as described below.

Interactive Infant NGT Systems

In alternative embodiments, an interactive NGT system of a smaller diameter and length may be used for providing nourishment to infants.

In embodiments, the infant single lumen NGT includes the position sensor to indicate proper positioning of the NGT. Additionally or alternatively, the infant NGT includes a nourishment sensor that senses when the stomach is full of nourishment.

Optic Sensors

In embodiments, the nourishment sensor may comprise a light source in conjunction with an optic sensor wherein the optic sensor provides positioning signals to the console.

In an exemplary embodiment of the optic sensor NGT system, a light source on a distal side of the tube provides light which is reflected from the GI tract to an optic sensor also mounted on the tube (or on another tube).

Optionally, the amount of light detected indicates the distance between the light reflecting off the GI tract and the optic sensor.

In an exemplary embodiment of the invention, the optic sensor collects light from a certain range of angles. Typically, as the GI wall is closer, more light will be reflected at those angles. Optionally, several optic sensors and/or light sources are provided on the circumference of the tube, so that narrowing is indicated by reduced reflections on several sides of the tube.

When the GI tract narrows, such as at the esophageal sphincter, the reflected intensity is expected to grow. For example, as the optic sensor passes through the esophageal sphincter, the reflected light is increased and the console apprises the operator of the proximity. The operator then advances the NGT forward through the sphincter, for example, a distance of between 1 and 10 centimeters to provide proper positioning.

Double Lumen NGT

Some embodiments of the interactive NGT system include a double lumen NGT in which the NGT includes a reflux-preventing/ameliorating sleeve, herein a reflux sleeve, around the nourishment tube.

During positioning, the operator slides the sleeve to the proper level within the esophagus. Optionally, some or all reflux expelled from the stomach is forced into the reflux sleeve, thereby preventing reflux from being aspirated.

In some embodiments, the reflux sleeve is connected to a reflux pump, alternatively referred to as a suction pump that is controlled by the above-noted controller. The reflux sleeve optionally includes a reflux sensor connected to the controller. Optionally, the reflux sensor is located near the end of the sleeve.

Other locations of the reflux sensor are contemplated as well, for example, at a distance from the end of the sleeve so if the sleeve is near the mid-esophagus, the reflux sensor is proximate to the pharynx.

When the controller receives sensor signals indicating gastric reflux, the console provides the above-noted audiovisual output and/or activates the reflux pump to provide negative pressure that evacuates reflux from the reflux sleeve and/or nearby esophagus.

Gastric Drip Protection

In an exemplary embodiment, during removal of the interactive NGT system, drips of nourishment and/or gastric contents from the end of the nourishment tube are prevented from contacting, and entering the trachea.

In an exemplary embodiments, the reflux sleeve (or a different sleeve, for example a close-fitting sleeve) protects the esophagus from such drips (e.g., from contact with caustic gastric acids that may cling to the outer surface of the nourishment tube), by surrounding the nourishment tube during removal.

Optionally, the suction pump is operated during nourishment tube removal. Optionally, a signal is provided to an operator when the nourishment tube is completely inside the reflux sleeve or completely out of the sleeve as only then would the reflux sleeve be retracted as well. Optionally, an outer drip preventing tube is provided even if no reflux pump is provided.

In some embodiments of the interactive NGT system (or non-interactive NGT system) a reflux sleeve 1, optionally close-fitting (alternatively not close-fitting) is mounted on a standard nourishment tube and provides various sensor functions, for example, as described herein.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring now to the drawings:

Overview of Double-Walled NGT

FIG. 1a illustrates an interactive NGT system 250 in accordance with one embodiment of the present invention. Interactive NGT system 250 comprises a double lumen NGT tube 5 including a suction sleeve 1 having an inner surface forming a luminal space that surrounds a nourishment tube 2. In some embodiments, the lumen of the inner tube is used for suction and the lumen of the outer sleeve is used for nourishment. In some embodiments, a single tube is used both for nourishment and for suction.

In one exemplary embodiment, NGT system 250 includes, inter alia, all of the following sensors. However, it should be understood that other embodiments may include only some or one or none of these sensors and/or use the sensors differently:

a position sensor 32 inside stomach a 209;
a nourishment sensor 4 above an esophageal sphincter 208;
a reflux sensor 3 in a mid esophageal location; and
an emergency sensor 31 in an upper esophageal position.

In use:

position sensor 32 indicates if the nourishment tube is inside the stomach;
nourishment sensor 4 indicates if nourishment is exiting outside the stomach;
reflux sensor 3 indicates the presence of reflux in the esophagus; and
emergency sensor 31 indicates if reflux is reaching a position where it might be aspirated.

In an exemplary operation, interactive NGT system 250 is inserted into the esophagus until position sensor 32 identifies the esophageal sphincter. Then NGT 5 is advanced until the tip of the nourishment tube 2 is in stomach 209 and feeding can commence.

Reflux, if it happens, may first be detected by nourishment sensor 4; in response to which a controller 14 may stop the nourishment and/or apply suction. After time, reflux may subside, as indicated by nourishment sensor 4, and feeding may commence, optionally according to a feeding plan and/or after a time delay.

In some cases, reflux may continue and reach reflux sensor 3. This may suggest the application of suction and/or removal of the nourishment tube 2 and/or application of suction. In some cases, reflux may continue more and reach emergency sensor 31. Optionally, the tube will be removed and/or suction applied. In some cases, a general alert may be sent to a caregiver, optionally at a remote station and/or using a more noticeable audiovisual signal.

In embodiments, positioning sensor 32, nourishment sensor 4, reflux fluid sensor 3 (alternatively referred to as gastric sensor 3) and/or emergency sensor 31 may be included alone or in various combinations in a single lumen NGT 5 or a double lumen NGT 5.

For example in administration of APIs, when there is no danger of reflux, double lumen NGT 5 may be equipped with nourishment sensor 4 to assure the user has received the API and/or that the tissue of stomach 209 is properly saturated with the API.

In some embodiments, one sensor can be used for multiple purposes. For example when position sensor 32 comprises a gastric fluid sensor, position sensor 32 may be used following positioning to detect gastric reflux in stomach 209.

Exemplary NGT System Sizes

Interactive NGT system 250 can be configured for use in adult human subjects; wherein, inter alia, the diameter and length of tubes 1 and 2 are sized to fit an adult human digestive tract. Alternatively, interactive NGT system 250 can be configured for use in children and/or infants, with appropriate diameters of suction sleeve 1 and tube 2.

In still further embodiments, interactive NGT system 250 can be configured for use in small animals such as a goose or even large animals, for example an elephant, with appropriate diameters of suction sleeve 1 and tube 2.

In adult human embodiments, a single lumen NGT 5 may have an outer diameter of between about 4 and 11 millimeters, with a wall thickness of between about 0.5 and 2 millimeters.

A double lumen NGT 5 may comprise a suction sleeve 1 having an outer diameter of between about 4 and 11 millimeters, with a wall thickness of between about 0.5 and 2 millimeters, and a luminal area of between about 10 and 18 millimeters squared or greater.

Nourishment tube 2 of double lumen NGT 5 may have an outer diameter of between about 1.5 and 5 millimeters, with a wall thickness of between about 0.25 and 1 millimeter. The lumen of nourishment tube 2 may be between about 1 and 3 millimeters, with a luminal area of between about 8 and 14 millimeters squared or greater.

An exemplary double lumen NGT may include:
i) an outer diameter of the outer sleeve of 7 millimeters;
ii) a lumen wall thickness of the outer sleeve of about 0.5 millimeters;
iii) an inner lumen diameter of the outer sleeve of about 6 millimeters;
iv) an outer diameter of the inner tube of about 5 millimeters; and
v) an inner lumen diameter of the inner tube of about 4 millimeters, such that the area of the inner tube is about 12.56637 millimeters Additionally, the exemplary double lumen tube may include optional spacers separating the outside of the inner tube from the inside of the outer tube, the spacers comprising one or more fins having a height of about 0.5 millimeters and a width of about 1.0 millimeters, such that the area of the outer tube is about 14.20796 millimeters.

A single lumen NGT 5 for an infant or a child typically has one of the following outer diameter measurements, s:

0-2 months 2-2.7 millimeters
3 months 2-2.7 millimeters
6 months 2.7 millimeters
1 year 2.7 millimeters
2 years 2.7 millimeters
3 years 2.7-3.3 millimeters
4 years 2.7-3.3 millimeters
5 years 3.3 millimeters
6 years 3.3 millimeters
7 years 3.3 millimeters
8 years 3.3 millimeters
9 years 3.3 millimeters
10 years 3.3-4 millimeters
11 years 3.3-4 millimeters
12 years 4 millimeters
13 years 4 millimeters In some cases, other sizes are used. The suction tube end is typically in the middle or upper third of the nourishment tube.

In some embodiments the walls of NGT 5 are thinner than the values above in order to increase flexibility. Additionally or alternatively, NGT 5 may incorporate more flexible materials to provide greater patient comfort.

While NGT 5 is shown passing through the patient nose, in some instances NGT 5 passes through the patient mouth, for example in the presence of trauma to the nose area. It should be understood that term nasogastric tube encompasses any tube that passes into a portion of the patient digestive tract, whether through the nose or through the mouth.

Figure 1B:
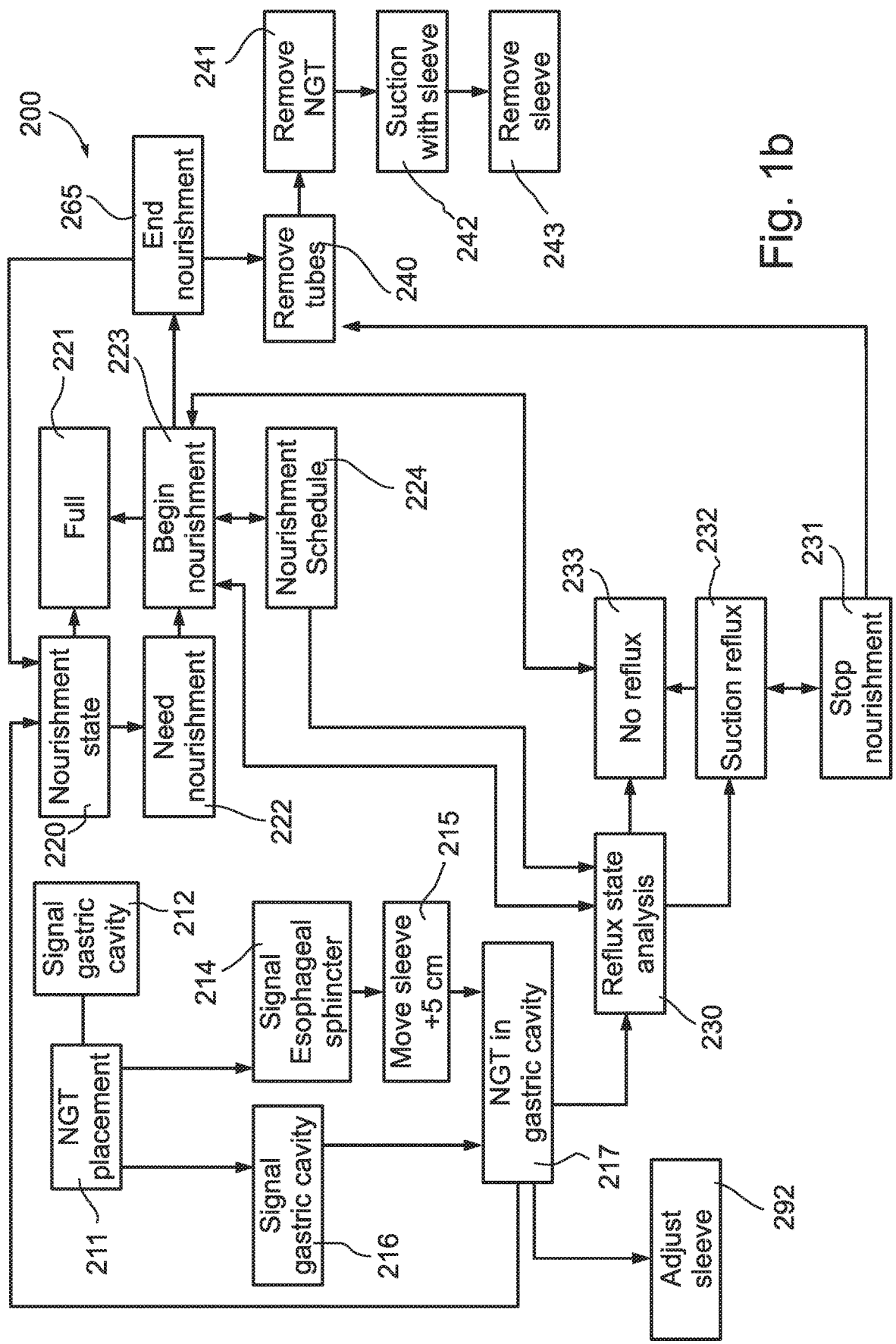
Figure 1C:
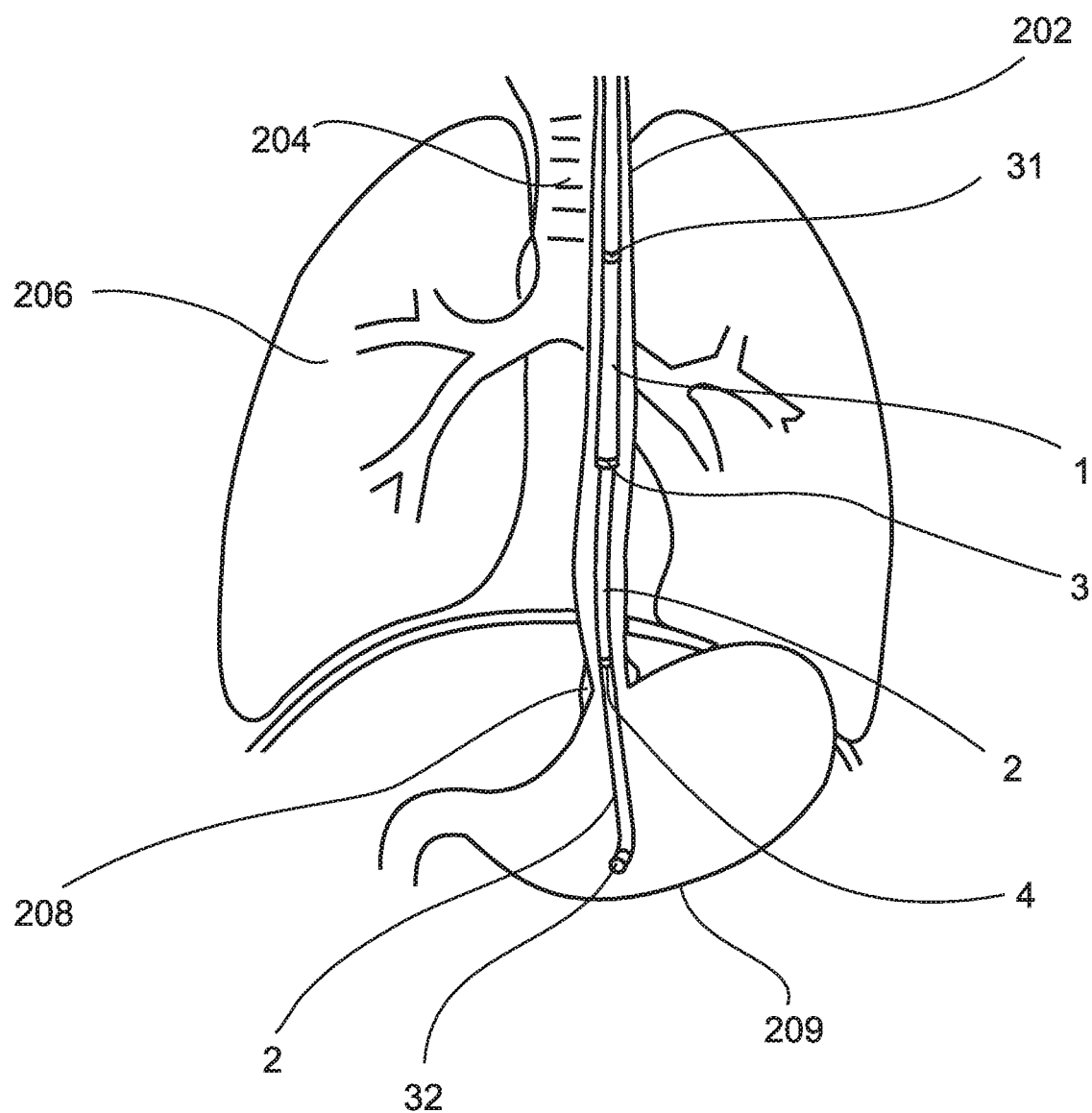

To better understand the many optional configurations of interactive NGT system 250, a flow chart is presented in conjunction with reference to structures shown in FIGS. 1a and 1c.

NGT Assembly Placement

FIG. 1b is a flow chart 200 showing exemplary operation of interactive NGT system 250 in various configurations thereof. In a placement stage 211, nourishment tube 2 is placed through an esophagus 202, esophageal sphincter 208 and into stomach 209.

At a positioning stage 212, position sensor 32 signals to gastric console 300, for example through audiovisual displays, that nourishment tube 2 is properly positioned in stomach 209.

In some embodiments, at a stage 214, position sensor 32 senses the proximity of esophageal sphincter 208 and a signal is provided through console 300, then caregiver push NGT 5 some more according to marks 199.

In some embodiments in which suction sleeve 1 is fixed in place along nourishment tube 2, prior to placement of NGT 5, measurements of digestive tract radiographs and/or MRI are taken. The operator then alters the length of nourishment tube 2 to ensure that the end of suction sleeve 1 is located an appropriate distance from esophageal sphincter 208 while nourishment tube 2 is contained within stomach 209.

Position sensor 32 may include any one of many types of sensors that will be further explained and illustrated below. Some of these sensors are optic sensors, electromagnetic sensors or other types of signal emitters and signal receivers.

The deployment of interactive NGT system 250 may vary considerably depending upon the type sensor used.

Optic Sensors

In a first sensor type and method for deploying interactive NGT system 250, position sensor 32 comprises the above-noted optic sensor.

When the sensor senses the esophageal sphincter 208, audiovisual displays on gastric console 300 signal the operator that position sensor 32 is proximate to esophageal sphincter 208 and the operator stops pushing NGT 5.

The operator may then tap esophageal sphincter 208 with the end of NGT 5 for tactile confirmation of position and then pass interactive NGT 5 through esophageal sphincter 208 an additionally approximately 5 to 10 centimeters into stomach 209.

Positioning Markers

In embodiments, interactive NGT system 250 is manufactured with at least one radiopaque distance marker. In other embodiments, interactive NGT system 250 is provided in a kit including a radiopaque marker that is placed in position by the operator.

Optionally, following placement of NGT 5, a radiograph is taken. The result provides the operator with an approximate distance that the end of interactive NGT system 250 should extend into stomach 209, and corresponding adjustments in the position of NGT 5 may be made by the operator Gastric Fluid Sensors In a second sensor type and method of deployment, position sensor 32 comprises a gastric fluid sensor.

The operator presses interactive NGT system 250 forward until position sensor 32 passes into stomach 209 and signals of the presence of gastric fluids. The operator then moves interactive NGT system 250 about 2 to 3 centimeters so that interactive NGT system 250 is properly positioned in stomach 209.

While the above methods have been directed to using, position sensor 32 in combination with nourishment tube 2, alternative methods utilizing nourishment sensor 4 may be used in positioning interactive NGT system 250.

Suction Sleeve Positioning

In an exemplary embodiment, nourishment tube 2 1 is retracted into suction sleeve 1 so that reflux sensor 3 is the most forward part of interactive NGT system 250.

The operator passes interactive NGT system 250 through esophagus 202 and into stomach 209.

Upon entering stomach 209, at a gastric cavity stage 216, signals from reflux sensor 3 sense the lower pH gastric fluids in stomach 209 and, via signals emitted, console 300 provides an appropriate signal to the operator at a stage 217.

While holding nourishment tube 2 in position, the operator retracts suction sleeve 1 about 5 to 20 centimeters so that reflux sensor 3 is located within esophagus 202, for example at about the middle of esophagus 202.

The operator optionally begins a stage 220 to determine nourishment state of gastric cavity.

Stand Alone Suction Sleeve

In another embodiment, in addition to sensing the lower pH of gastric fluids, reflux sensor 3 senses the higher pH of post prandial nourishment mixed with gastric fluids.

Initially, the patient receives nourishment through a stand alone nourishment tube 2, after which nourishment tube 2 is removed from the patient.

A stand alone suction sleeve 1 is then pushed by the operator through esophagus 202 until reflux sensor 3 senses post prandial nourishment in stomach 209. Console 300 emits an audiovisual signal that interactive NGT system 250 is properly positioned and suction sleeve 1 is left in position until the danger developing post prandial reflux has passed.

NGT Position Markers

As noted above, a variety of methods may be deployed to ensure proper positioning of NGT 5.

In another positioning embodiment, suction sleeve 1 and/or nourishment tube 2 include external markings 199 so that the operator is apprised of the length of suction sleeve 1 that has been placed through esophagus 202 to determine when nourishment tube 2 is positioned in stomach 209 and/or when suction sleeve 1 is properly positioned in esophagus 202.

Providing Nourishment

In embodiments, at a stage 220, nourishment sensor 4 signals to gastric console 300 the state of nourishment in stomach 209. For example at a stage 221, nourishment sensor 4 senses nourishment above esophageal sphincter 208 and signals that stomach 209 is full, and gastric console 300 ceases providing nourishment.

Alternatively, upon receiving sensor signals that stomach 209 is empty or partially empty, gastric console 300 continues to provide nourishment through tube 2 at stage 223.

Alternatively, at a stage 222, console 300 receives signals that stomach 209 is empty or partially empty and additionally senses that either nourishment is no longer passing through nourishment tube 2 or, through an additional sensor, that the nourishment container is empty.

If the source of nourishment has been exhausted and the patient nourishment schedule requires additional nourishment, console 300 optionally signals the operator to replace the empty nourishment container with a new container.

If, on the other hand, console 300 senses that nourishment is no longer passing through nourishment tube 2, in spite of the fact that the proper amount of nourishment has not been dispensed, console 300 optionally signals the operator to check and fix a blockage, for example a kink in nourishment tube 2.

Ex Vivo Nourishment Sensors

While nourishment sensor 4 is shown as a part of nourishment tube 2, there are many alternatives that are contemplated and may be used in with interactive NGT system 250; the following being just some of the many alternatives.

For example, in some embodiments, interactive NGT system 250 includes an ex vivo stomach impedance sensor that uses stomach impedance and/or impedance of gastric contents within esophagus 202 as an indication that stomach 209 is full.

In another example, nourishment sensor 4 includes a myographic and/or electrical activity sensor that senses activity of stomach 209 indicating digestion, emptiness and/or fullness.

As noted above, NGT 5 may provide and track nourishment in the form of an API; the following being but a few examples of API dispensing embodiments.

Dispensing an API

By way of example, in a case wherein an antacid API is delivered to stomach 209, at nourishment state stage 220, nourishment sensor 4 is configured to detect, for example, the amount of antacid that is residing in stomach 209. In the event that antacid is lacking, at stage 223, gastric console 300 provides additional antacid to stomach 209 via nourishment tube 2.

In detecting the presence of antacid, for example, the API may be doped with biocompatible materials, for examples dyes and/or ultrasound-reflecting molecules, with nourishment sensor 4 being configured to sense such materials.

In alternative embodiments, nourishment sensor 4 may be configured to directly sense the pH of the antacid.

In some embodiments, the API may comprise a lifesaving local antibiotic that must reach a specific tissue saturation level to be effective; and nourishment sensor 4 may directly sense a tissue state of stomach 209.

For example nourishment sensor 4 may include light source which reflects light off the tissue of stomach 209 and is received by nourishment sensor 4. Signals related to, for example, the spectrum reflected from the tissue, are then sent to gastric console 300 and analyzed to determine whether the tissue of stomach 209 includes a proper saturation of the administered API.

In embodiments, the API is mixed with a dye that adheres to mucus in the digestive tract and nourishment sensor 4 tracks the concentration of the dye via spectral analysis.

Optionally, prior to dispensing the API combined with a dye, interactive NGT system 250 and/or stomach are optionally flushed with saline and/or sterile water to facilitate accurate readings of API concentration.

Optionally, when the patient has received the proper amount of nourishment, or nourishment sensor 4 signals that stomach 209 is full at full stage 221, gastric console 300 proceeds to an end nourishment stage 265 and provision of nourishment is stopped.

Reflux Detection

In some situations, for example during the administration of nourishment, stomach 209 may expel gastric acid, and reflux sensor 3 and/or nourishment sensor 4 sense excess gastric acid in esophagus 202 at a stage 230 to alert gastric console 300.

At a suction reflux stage 232, gastric console 300 enters a stop nourishment stage 231 and activates a pumping assembly (FIG. 4) that provides negative pressure through suction sleeve 1 to suck gastric fluid from esophagus 202, thereby removing the cause of reflux. Causes of reflux may include gastric acid accumulation in stomach 209, causing gastric muscle spasm and discharge of gastric contents.

Alternatively, overfilling of stomach may result in gastric content discharge or patient condition results in a tendency toward expelling gastric contents.

Alternatively, gastric fluid pressure from stomach 209 on contents of esophagus 202 may be responsible for reflux; such pressure being caused in some cases by entry of nourishment into stomach 209. In cases where reflux occurs during nourishment, upon detection of reflux fluid, gastric console 300 stops all nourishment at stage 231 until reflux sensor 3 and/or nourishment sensor 4 signal that esophagus 202 is clear of gastric fluid at a no reflux stage 233.

Optionally, following cessation of nourishment, a stage 240 is accessed wherein all tubes are removed from the patient and oral feeding, for example, is resumed.

As noted, reflux is assessed once NGT 5 prior to dispensing nourishment following clearance of reflux. However, interactive NGT system 250 additionally may be configured to access stage 230 to determine the presence of reflux prior to beginning dispensing nourishment at a given feeding.

Nourishment Scheduling

Optionally, gastric console 300 includes a programmable nourishment scheduler and at a stage 224, nourishment is provided according to the parameters of the nourishment schedule that has been programmed into the scheduler. For example, console tracks the amount of nourishment provided to the patient. If nourishment is stopped due to reflux, upon resumption of nourishment, console 300 stops the nourishment when the patient has received the amount of nourishment required for the given feeding.

In some embodiments, console 300 is optionally connected to an intravenous nourishment supply and includes a calorie counter. During the stopped feeding period, the intravenous nourishment continues and console 300 counts the calories of nourishment dispensed. Upon resumption of feeding via nourishment tube 2, console 300 keeps track of the IV feeding calories dispensed and stops dispensing nourishment via nourishment 2 when the total caloric allotment to the patient, including IV-dispensed calories, has been reached.

In addition, console 300 optionally is configured to be programmed to record and/or modify nourishment based upon real time and/or historic patient information.

In one example, console 300 may dispense nourishment at a rate of 10 cubic centimeters per minute throughout a feeding.

If the patient develops reflux at a given feeding, for example half way through the feeding, console 300 may automatically reduce the rate of nourishment dispensation at the beginning of the next feeding or around half way through the feeding, thereby reducing the chances for reflux recurrence.

Additionally or alternatively, interactive NGT system 250 may be configured with multiple nourishment sources contained separately within different containers. Optionally, a fluid switch (e.g., electrically controlled) is provided for selecting which source will feed the nourishment tube. Alternatively, two or more sources may be mechanically connected to a same feeding tube, optionally, with one way valves to prevent backflow. As but an example of the many possibilities, a first source may contain an API against stomach acid; a second source may contain nourishment; and a third source may contain vitamin supplements.

In such embodiments, all containers may be connected via console 300 and console 300 optionally includes dispensing information on each of the nourishment sources.

In some embodiments, nourishment tube 2 comprises multiple lumens either side-by-side or axially located and console 300 is configured to dispense nourishment from the various sources.

In some situations, stomach 209 spastically contracts with sufficient force to cause large volumes of gastric fluid to pass through esophagus 202, possibly overpowering the ability for suction sleeve 1 to suck up all gastric fluid. The following embodiment is configured to deal with such emergencies.

In embodiments the interactive NGT system can be manufactured to fit on to existing feeding and suction machines. In such embodiments the NGT system includes one or more of the following features:

1. The suction sleeve is configured to tightly surround a standard NGT.
2. The NGT is configured to connect to a standard feeding machine, for example, the Novartis Compat Enteral Feeding Pump.
3. An actuator is placed on a tube that provides food, for example between a food source and a food pump or between a food source and a body. In one example, the actuator is a tube pincher which selectively pinches the tube and prevents food flow therethrough. In another example, the actuator is a peristaltic pump. In an exemplary embodiment of the invention, the actuator is a linear actuator which closes the tube when reflux is detected, optionally by a reflux detecting sensor.

In an exemplary embodiment of the invention, an add-on to a standard feeding machine is as follows:

a) mount a suction sleeve with inward fins on a standard feeding tube.

b) connect sleeve and tube to a T junction that separates the feeding tube from the suction sleeve; optionally the input to the T junction comprises two coaxially tubes, one leading to one side of the junction and one leading to the other side of the junction. Optionally the body of the T junction forms one of the coaxial tubes, for example the suction sleeve.

c) connecting a tube from the T junction to a standard feeding machine, for example the Novartis Compat Enteral Feeding Pump.

d) connect a tube from the T junction to a standard suction machine for example, the DeVilbiss Homecare Suction Pump. Alternatively a suction source in this or in other embodiments comprises a standard suction portion, optionally with a disposable or washable waste filter mounted thereon.

e) mount an actuator, for example a linear actuator, on the feeding tube for example between the feeding source material and the feeding machine; the actuator optionally controlled by the console or by a provided controller.

f) Optionally, when a sleeve ring, located above the esophageal sphincter, detects reflux, the sleeve ring signals the console which then causes the linear actuator to close the passage of food and food will cease being dispensed to the patient.

g) Optionally, when reflux is detected, the console will activate the suction pump. Optionally, the console selectively provides AC power to a mains cable of the suction pump, which is always on.

Alternatively, the console may provide alternative power sources, for example DC power.

Emergency Reflux Sensor

In some embodiments, suction sleeve 1 additionally includes emergency sensor 31 that is activated when reflux has passed beyond suction sensor 3, indicating that aspiration of gastric contents may imminently occur.

In such cases, gastric console 300 receives a signal from emergency sensor 31 and provides, inter alia, audiovisual signals that alert an operator that aspiration alleviating steps must immediately be taken, beginning with, for example, removing nourishment tube 2.

In some embodiments, interactive NGT system 250 includes a retraction assembly, for example a motor that immediately retracts nourishment tube 2 from the patient, thereby enlarging the effective diameter of the lumen of suction sleeve 1 and reducing the chance for aspiration. In some protocols, console 300 automatically activates the pump attached to reflux sleeve 1 and begins reflux evacuation. Console 300 then alerts the operator of the retraction and reflux suction and the necessity to take further action, for example to inspect the mouth and remove any accumulated reflux.

NGT Assembly Removal

After treatment, for example when the user no longer requires nourishment and/or reflux danger has passed, the operator optionally chooses remove tubes stage 240, after which NGT 5 is removed at a stage 241.

In the first step of removing tube 2, suction sleeve 1 is typically activated, and optionally remains activated during the entire procedure. At a stage 242, after tube 2 is removed, any gastric contents on the outside of suction sleeve 1 are sucked by gastric pump, rather than remaining in esophagus 202.

In the second step, at a stage 232 after tube 2 is removed, reflux sensor 3 and or emergency sensor 31 signal gastric console 300 that gastric fluid is not present in esophagus 202, and suction sleeve 1 is removed safely at a stage 243.

NGT Assembly Sensors

Figure 2:
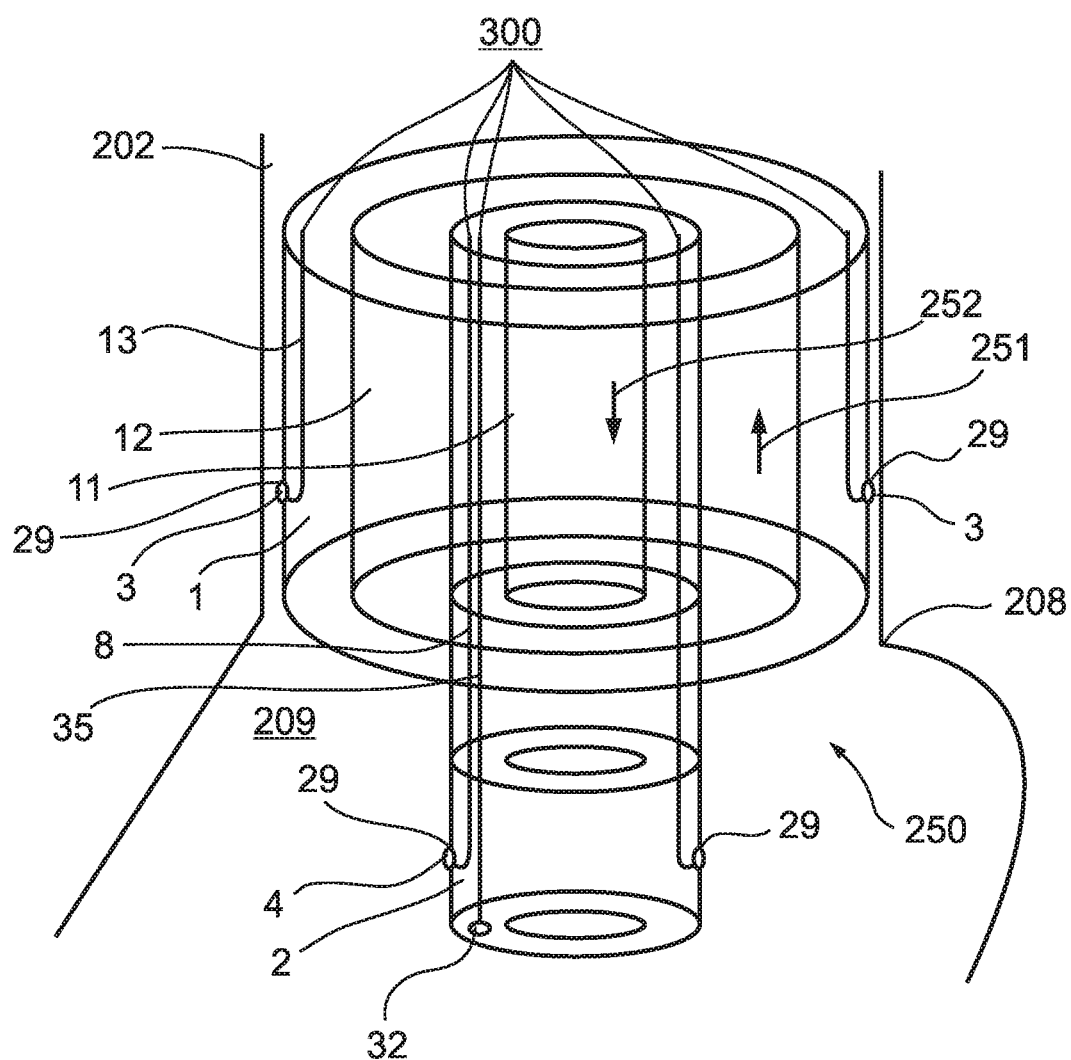

FIG. 2 shows a schematic representation of a portion of interactive NGT system 250 in vivo, indicating various sensors attached thereto. Gastric fluid 12 is being evacuated from stomach 209 in a direction 251 in suction sleeve 1 while nourishment 11 is being dispensed into stomach 209 in a direction 252.

Gastric console 300 is connected to:
 i) nourishment sensor 4 via a nourishment connector 8;
 ii) reflux sensor 3 via a fluid connector 13; and
 iii) Positioning sensor 32 via positioning connector 35.

In alternative embodiments, nourishment sensor 4, reflux sensor 3 via a fluid connector 13 and positioning sensor 32 include wireless transmitters and wirelessly transmit signals to console 300 instead of via connectors 8, 13 and 35.

Electrical resistance and/or impedance is optionally used to characterize whether a fluid is comprised of saliva or gastric contents and can be measured along openings 29 as well as other methods described below.

As described below, the present invention, in some embodiments thereof, contemplates a gastric console that provides a variety of nourishment and safety functions.

Gastric Console

Figure 3:
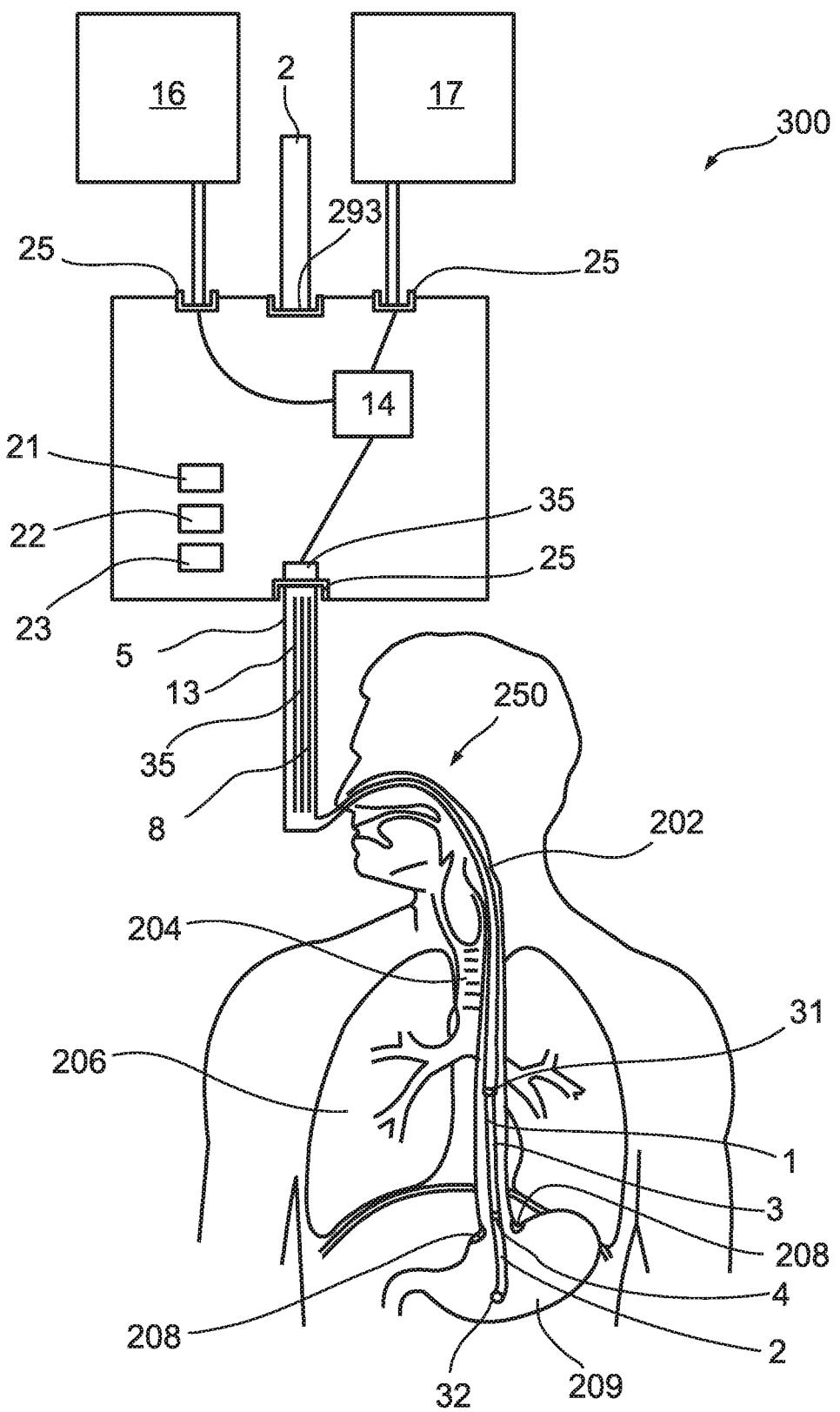

As shown in FIG. 3, gastric console 300 houses a controller 14, comprising a central processing unit (CPU)

including hardware and/or software modules to control a variety of functions provided by gastric console 300.

For example, controller 14 controls the actions of a suction pump 16 and a nourishment pump 17 which are connected to gastric console 300 by tube connectors 25. Connectors 25 optionally allow easy disassembly of suction pump 16, nourishment pump 17 and/or NGT 5 from gastric console 300 for cleaning or exchange.

Gastric console 300 additionally includes audiovisual displays, herein signalers 21, 22 and 23, which may comprise audio outputs such as speakers, a variety of lights, for example LEDs of various colors. Alternatively, signalers 21, 22 and 23 may comprise one or more display screens that display text messages.

Just some of the many indications provided by signalers 21, 22 and 23, may include:

1) A nourishment signaler 21 signals the operator that nourishment is being provided to the user. Upon detection of reflux fluid by reflux sensor 4, alternatively referred to as "gastric fluid sensor" 4, nourishment signaler 21 optionally signals the presence of reflux and stops the feeding.

2) A suction signaler 22 signals, upon detection of reflux fluid by reflux sensor, the start of suction pump 16 to evacuate gastric fluid from esophagus 202.

3) A danger signaler 23 signals that externally positioned emergency sensor 31 has detected reflux in the upper part of esophagus 202 and that the operator must immediately pull out nourishment tube 2; thereby increasing the available space and diameter in suction sleeve 1 so that the pressure on gastric fluid decreases. Decreased pressure can prevent gastric fluid from passing into trachea 204 and being aspirated by lungs 206.

In some embodiments, gastric console is connected to additional sensors, for example a pulse sensor and/or other physiological information, and displays such information on one or more of signaler 21, 22, and 23. Optionally, a feeding program is related to such physiological information, for example, feeding when a patient is awake, based on a blood pressure thereof.

Figure 12:
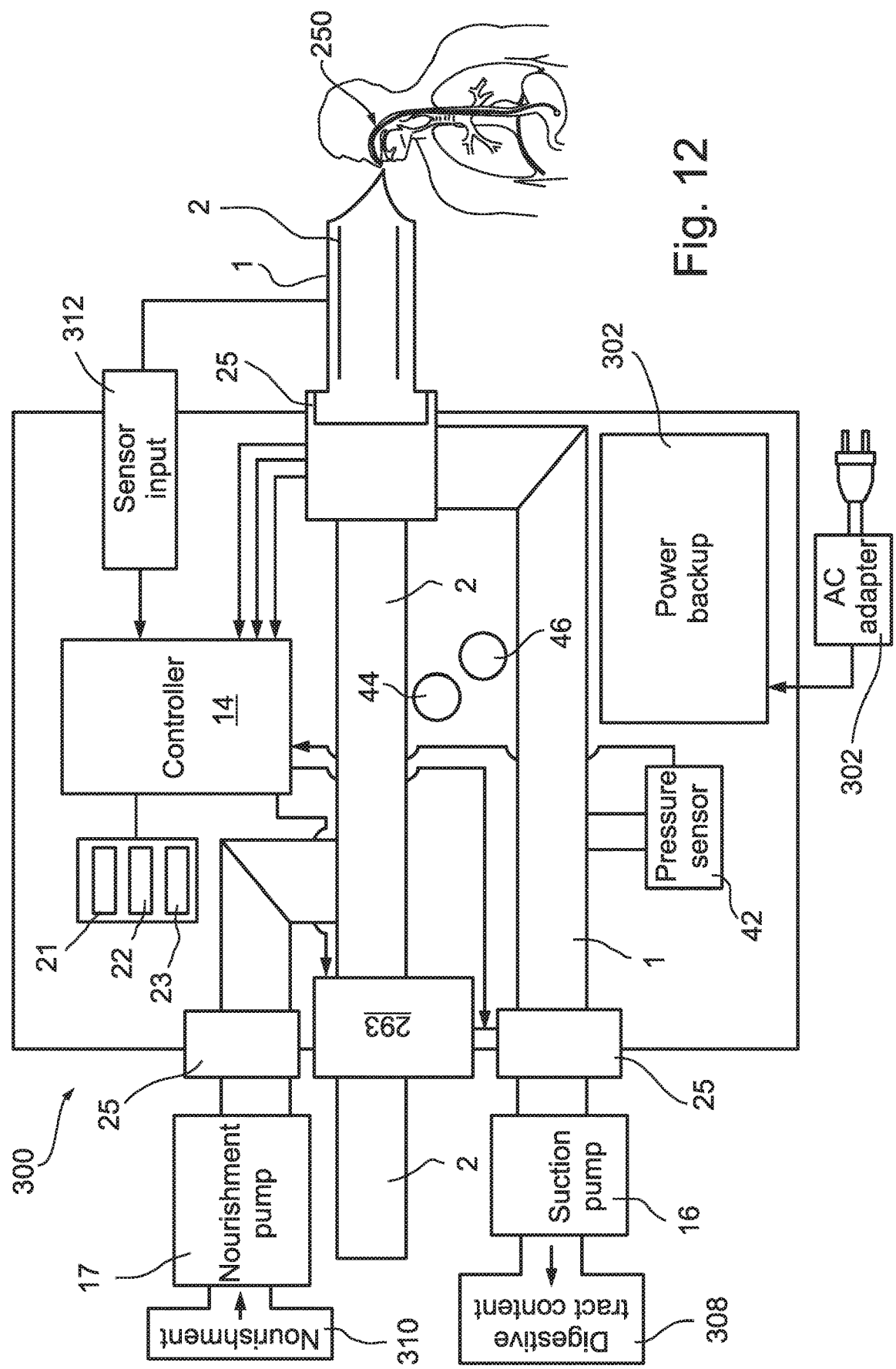

FIG. 12 is a detailed view of gastric console 300 in which gastric console 300 optionally includes an AC adapter 302, power backup 302, nourishment container 310 and reflux container 308 in which digestive tract content is stored. The input of one or more of the above-noted sensors is indicated at sensor input 312.

In embodiments, gastric console 300 includes a pressure sensor 42 that detects the pressure in suction sleeve 1. A pressure increases above a preset level may indicate that at least a portion of esophagus 202 has collapsed around suction sleeve 1.

In such instances, controller 14 will optionally reduce the pumping pressure or cease the pumping of suction pump 16.

Signaler 22 provides an audiovisual signal that the patient must be inspected by the operator to determine if the collapse of esophagus 202 is related to alternative conditions, for example a cardiovascular accident that has caused the patient body to enter one or more stages of shock, followed by shutdown of one or more vital systems.

There are many additional features that may be incorporated into interactive NGT system 250, the following features being just of few of the many possibilities.

Optional Additional Console Features

In embodiments console includes a nourishment pullout connector 293 that allow an operator to remove nourishment tube from the patient without removing suction sleeve 1, a possibly necessity when reflux is detected.

Pullout connector 293 surrounds a portion of nourishment tube that protrudes above console 300 and, to individually remove nourishment tube 2, the operator presses pullout connector 293 and pulls nourishment tube 2 upwards, until fully outside the patient.

Optionally, console 300 includes a tube retractor unit 44 that includes a motor that automatically pulls nourishment tube 2 out of the patient upon detection of reflux. Additionally or alternatively, tube retractor unit 44 pulls nourishment tube 2 out of the patient upon activation by the operator.

In some embodiments, console 300 may include a sleeve retractor 46 that retracts reflux sleeve 1 out of the patient, for example after nourishment tube 2 has been pulled out at the end of feeding; either automatically or upon activation by the operator.

In embodiments, tube connectors 25 are shaped so that, when interactive NGT system 250 is provided as a complete stand alone system, the operator cannot accidently connect a standard NGT tube to console 300.

Spacers

Figure 4:
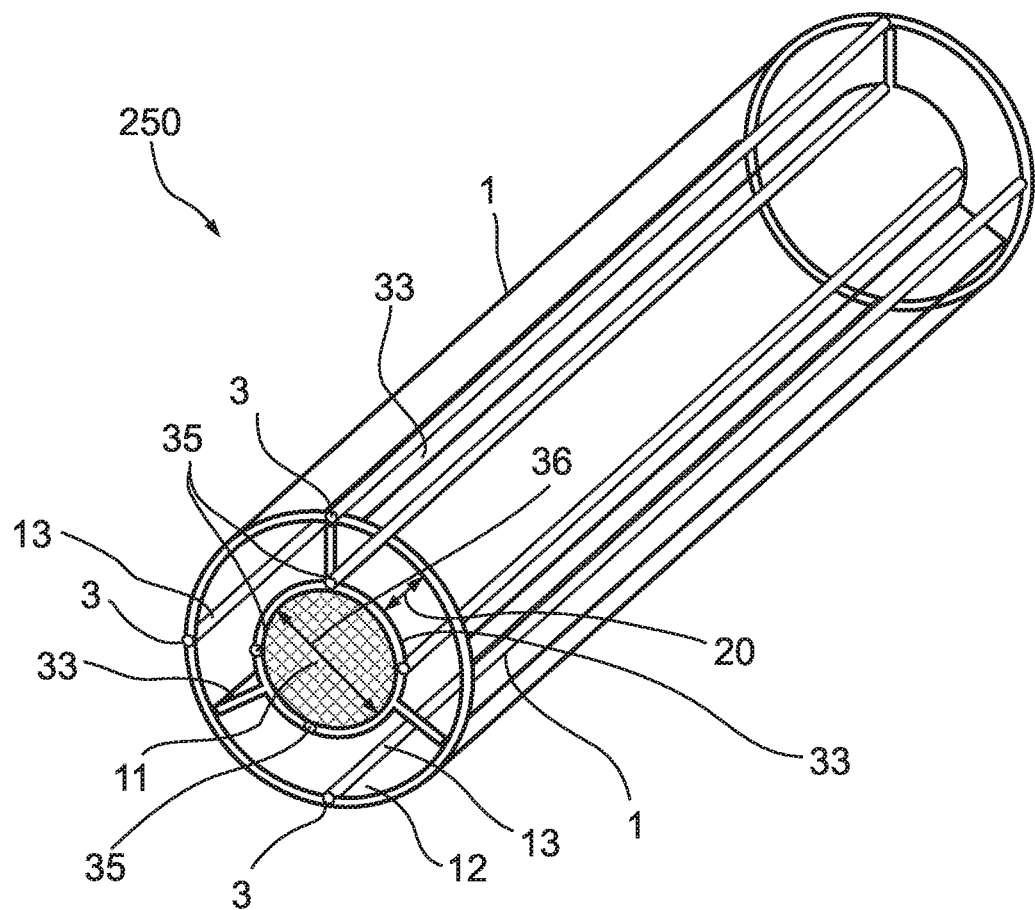

Optionally, one or more spacers, alternatively referred to as spacer elements or fins, are provided to space suction tube 1 from nourishment tube 2. Optionally, the spacers comprise one or more fins, however, other shapes, such as a plurality of rounded projections on one or both of the sleeves, may be used. FIG. 4 is a cut-away view of interactive NGT system 250 in which optional spacers 33 project radially outward from nourishment tube 2, which is filled with nourishment 11; an embodiment that may be used when interactive NGT system 250 is provided as a stand-alone system. In other embodiments, optional spacers 33 project radially inward from suction sleeve 1 allowing suction sleeve 1 to be fitted onto an existing nourishment tube 2. Alternatively, in embodiments where Interactive NGT 250 system is provided as stand-along system, spacers 33 may be located on nourishment tube 2.

In embodiments, nourishment tube 2 or sleeve 1 include tracks for guiding spacers 33 which project from sleeve 1 or nourishment tube 2, respectively.

Additionally, spacers 33 may be elastic and/or collapsible, and may extend the entire length of sleeve 1 or nourishment tube 2 or only along a portion of sleeve 1 or nourishment tube 2 and/or may be continuous or interrupted (e.g., 2, 4, 10, 20 times or more along their length.

It should be noted that in a dual lumen NGT 5, the presence of spacers 33 may add stiffness that can be reduced by the above-noted configurations in which NGT 5 is thinner and/or manufactured from materials having greater flexibility that those of a standard NGT.

Figure 5:
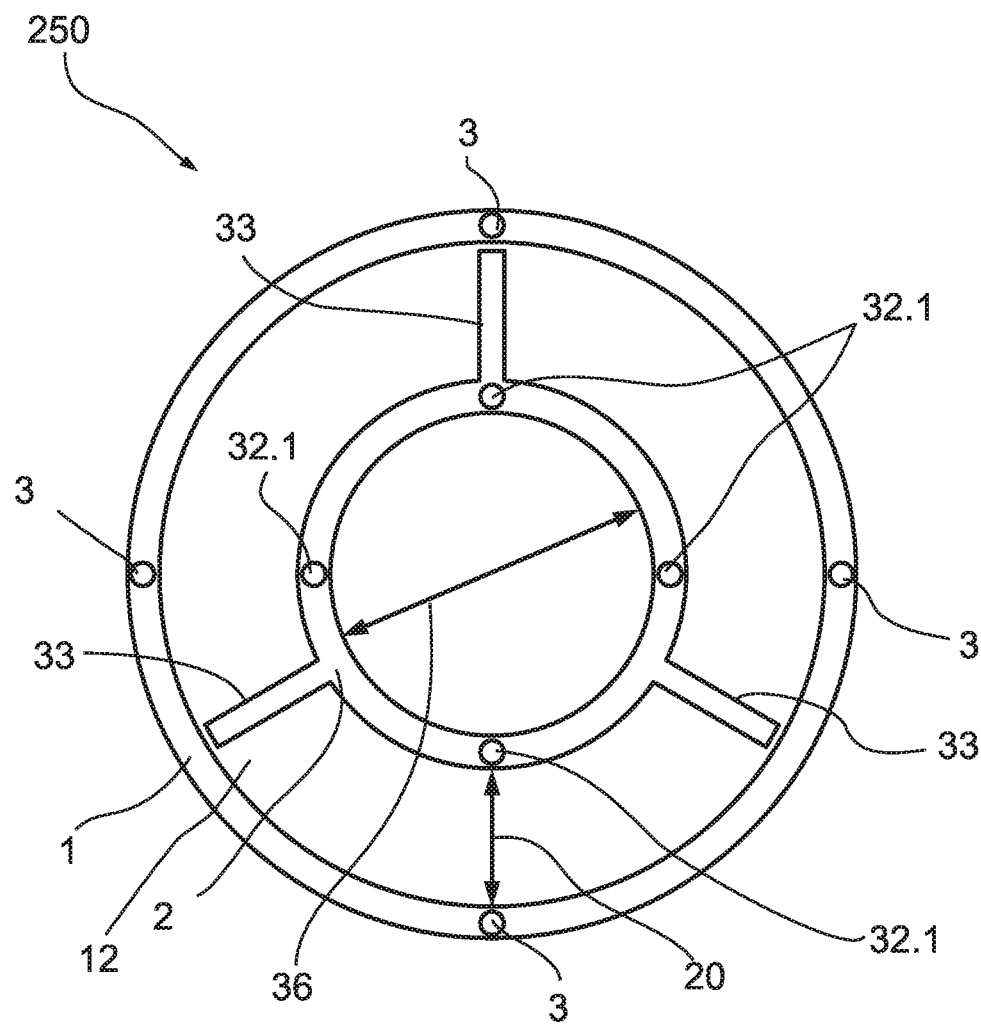
Figure 6:
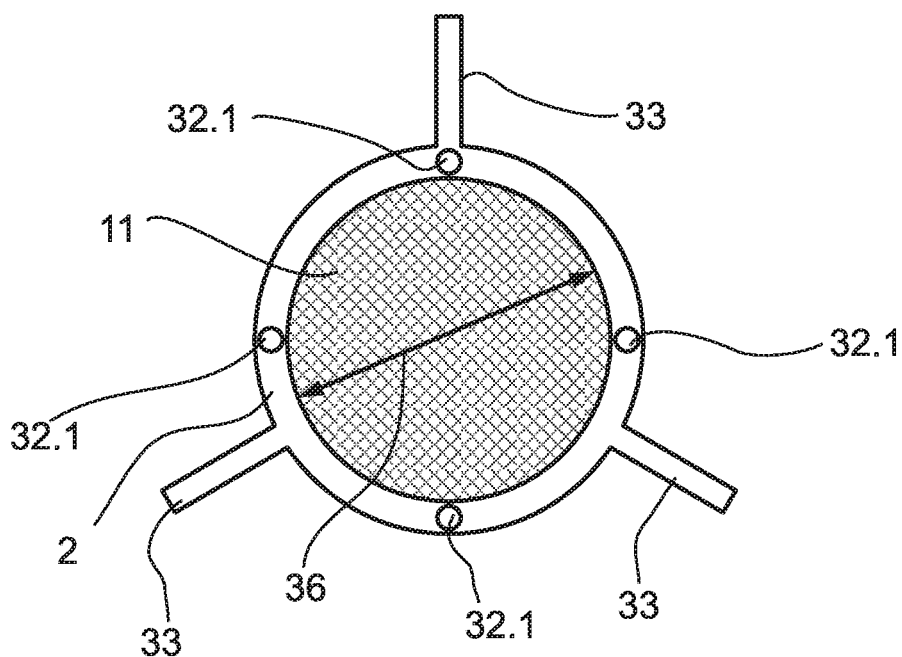

FIGS. 5-6 are a cross sectional and a side view, respectively, of the interactive NGT system 250 shown in FIG. 4 in which a distance 20 between nourishment tube 2 and suction sleeve 1 contains gastric fluid 12, while nourishment tube 2 comprises diameter 36 containing nourishment 11.

In embodiments, diameter 36 is approximately the same as distance 20. In further embodiments, diameter 36 is greater or less than distance 20.

There are many enhancements that may be contemplated for interactive NGT system 250, the following being but a few of the many possibilities.

NGT Options

Figure 7A:
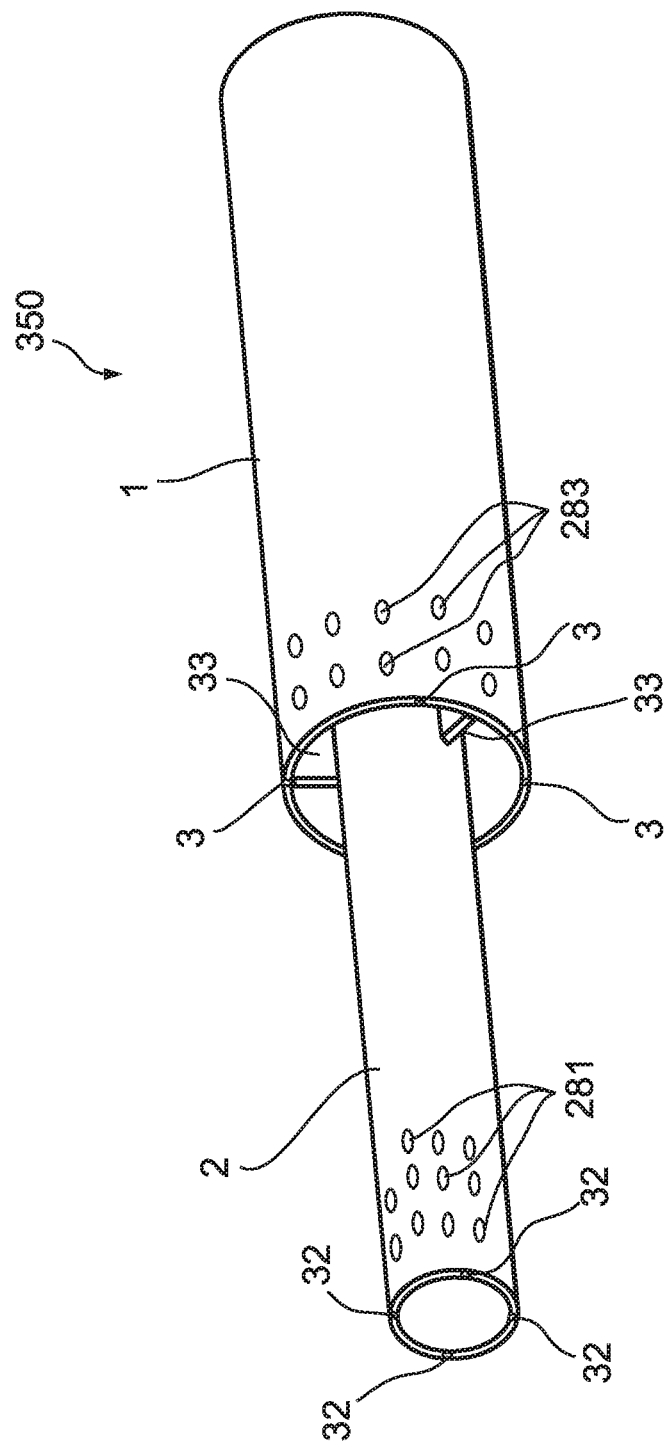

FIG. 7a shows an interactive NGT system 350 in which suction sleeve 1 includes side suction openings 283 to increase the area through which suction is applied, thereby possibly reducing the chances that the esophagus will collapse around suction sleeve 1.

Alternatively or additionally nourishment tube 2 includes optional side openings 281 to facilitate dispensation of nourishment.

Add-on Suction Sleeve

Figure 7B:
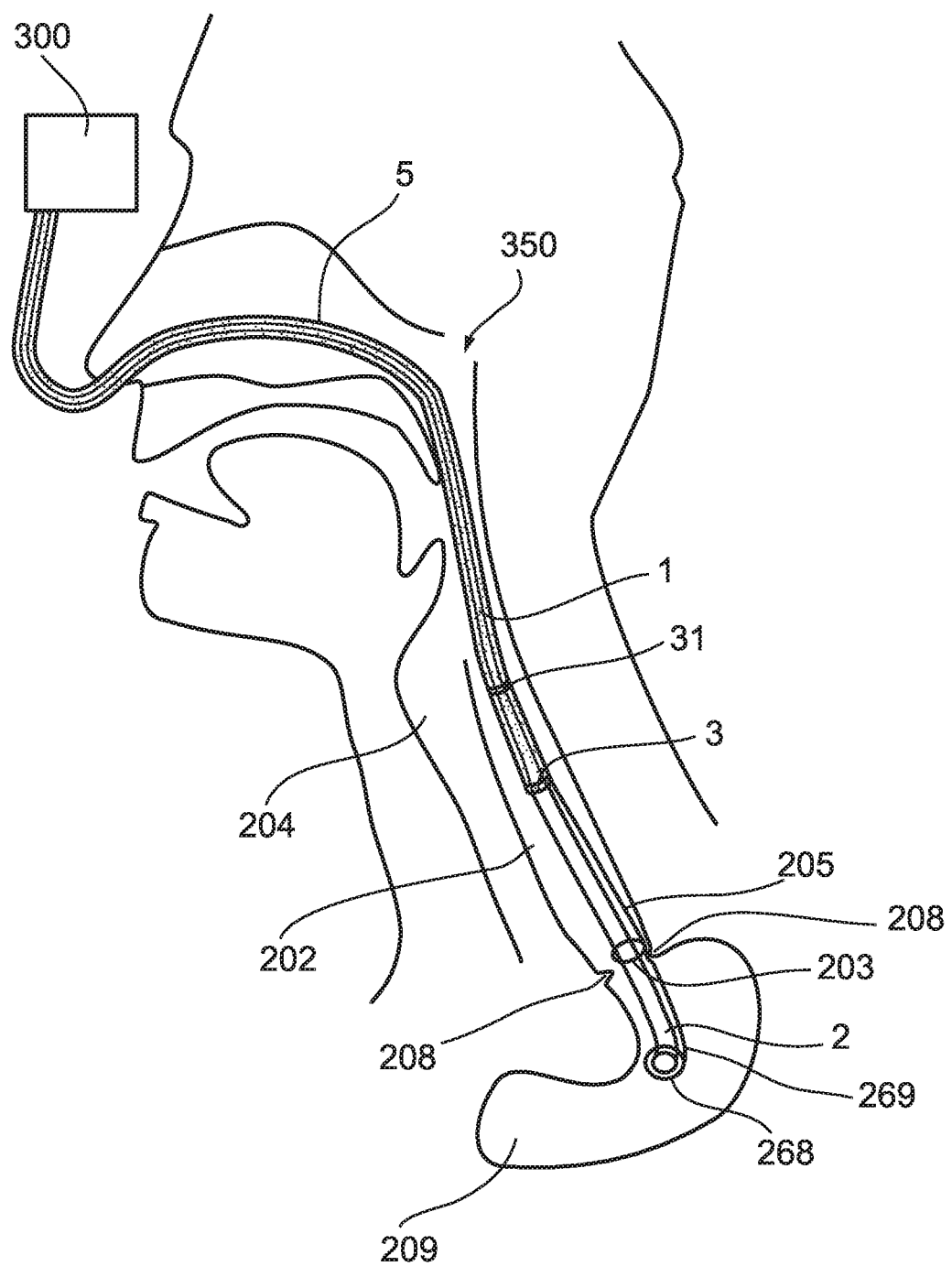

In some embodiments, for example, as seen in a schematic view of interactive NGT system 250 in FIG. 7*b*, suction sleeve 1 includes a nourishment sensor ring 203 connected to console 300 via a nourishment connector 205; and a positioning ring 268 connected to console 300 via a positioning connector 269.

Optionally, suction sleeve 1 additionally includes reflux fluid sensor 3, and/or emergency sensor 31 as noted above.

Figure 8:
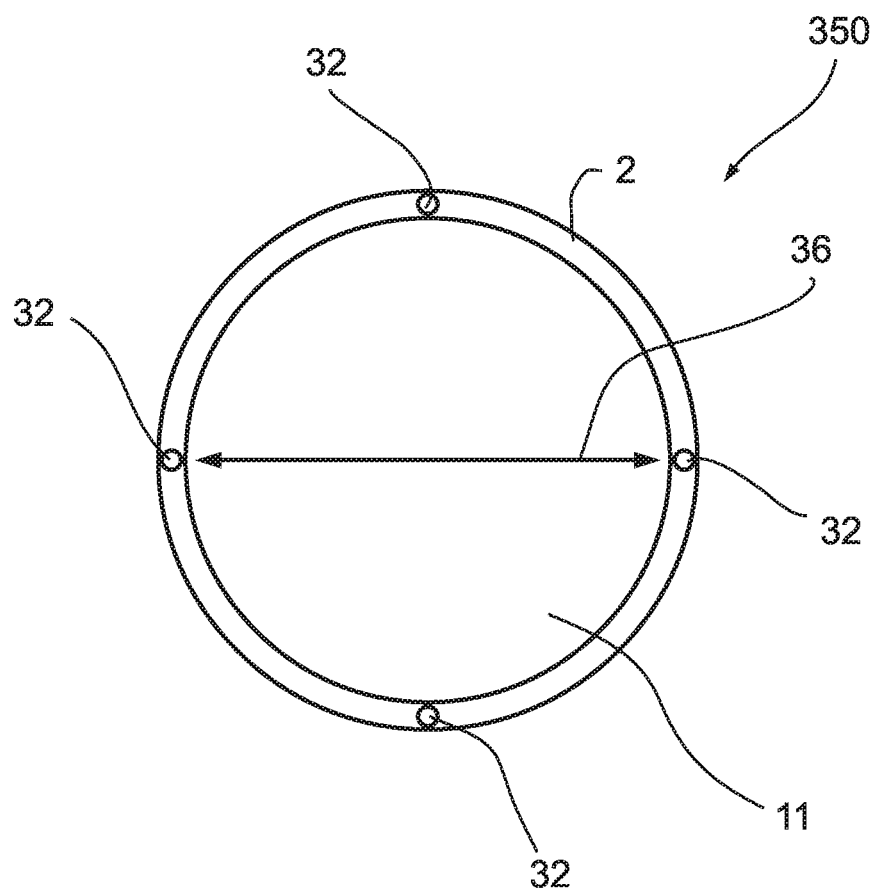

In the embodiment shown, interactive NGT system 350 may comprise a standard nourishment tube 2 around which suction sleeve 1 is fitted, thereby allowing, for example, a care-providing institution to reduce costs in providing interactive NGT system 350. FIG. 8 shows nourishment tube 2 of interactive NGT system 350 filled with nourishment 11.

There are many types of sensors that can be used in conjunction with nourishment tube 2 and/or suction sleeve 1. The following examples describe just some of the many types of sensors that can be utilized.

Alternative Sensors

Figure 9A:
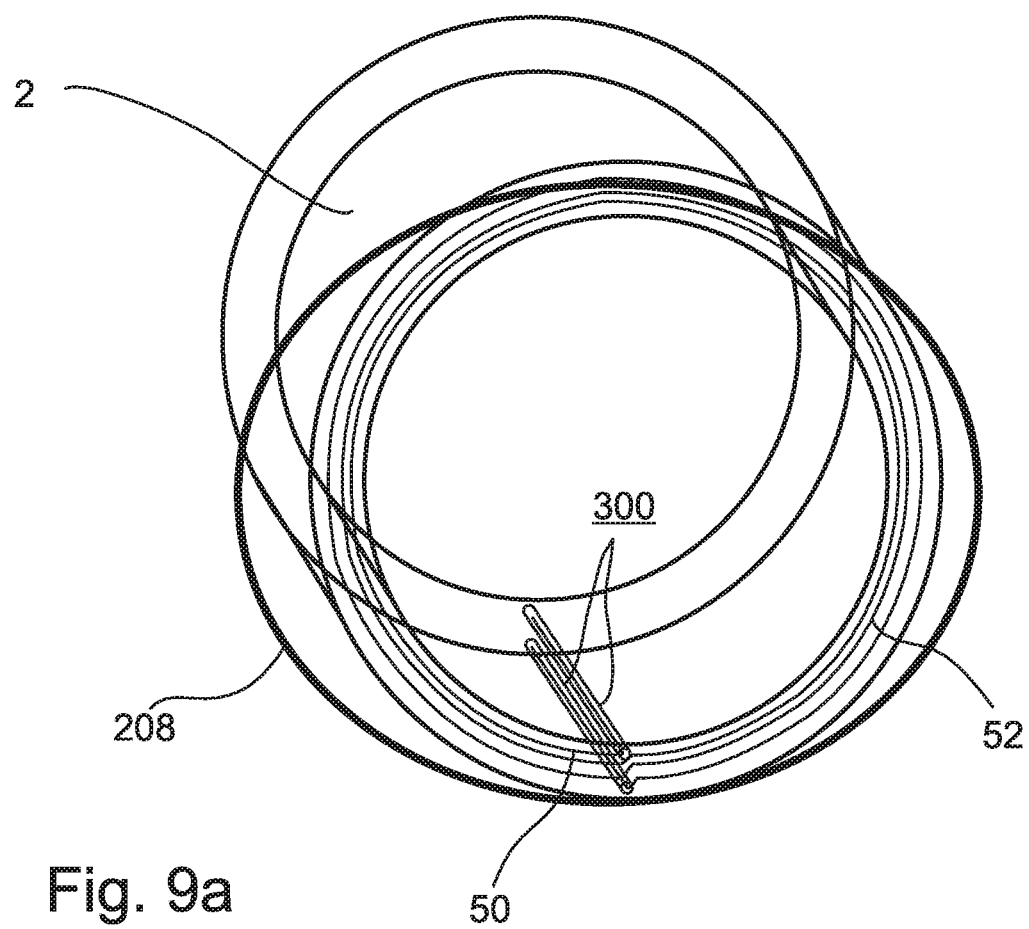
Figure 9B:
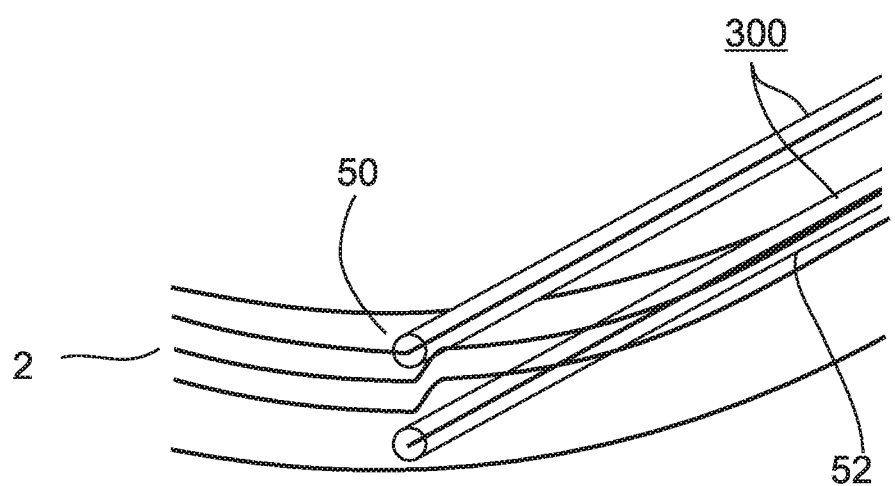

FIGS. 9*a* and 9*b* show an antenna sensor 50 comprising an electromagnet coil 52 which emits signals and detects the return signals which are interpreted by gastric console 300 to determine the distance of nourishment tube 2 from the esophageal sphincter 208 noted above.

Fiber Optic Sensors

Figure 10:
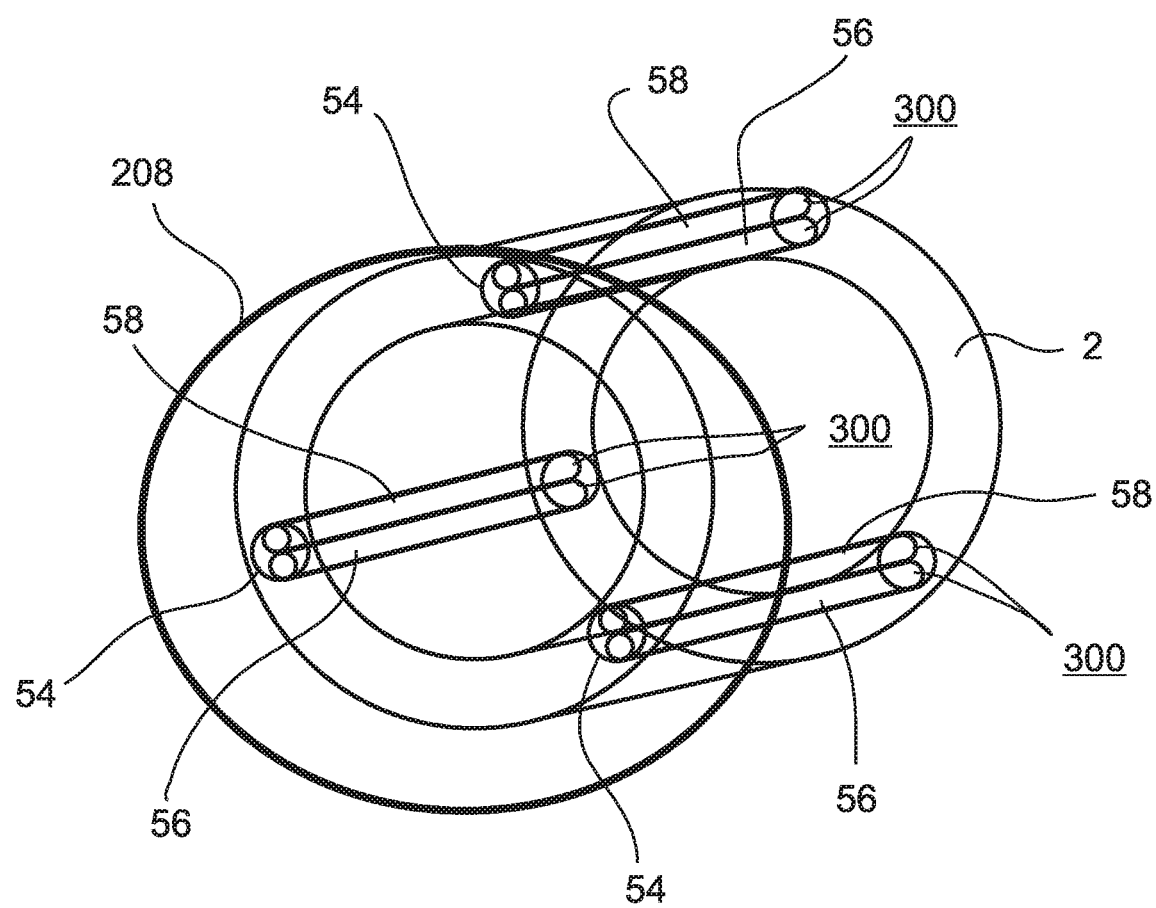

FIG. 10 shows a portion of nourishment tube 2 including fiber optic sensors 54 comprising a light-transmitting fiber 56 which transmits light that reflects off esophageal sphincter 208 and a light-receiving fiber 58 that receives the reflected light. As optic sensors 54 approach esophageal sphincter 208 the reflected light received by receiving fiber 58 increases. The magnitude amount of light received by receiving fiber 58 is interpreted by gastric console 300 to apprise the operator of the distance between nourishment tube 2 and esophageal sphincter 208.

While three sets of light-transmitting fiber 56 and light-receiving fiber 58 are shown as pointing forward on the tip of nourishment tube 2, alternative configurations are contemplated. For example, to enhance sensor sensitivity in the presence of food particles that block light transmission and/or receiving, as many as 10 or even 20 light-transmitting fibers 56 and/or light-receiving fibers 58 may be included in nourishment tube 2.

Alternatively or additionally, some, or all of light-transmitting fibers 56 and/or light-receiving fibers 58 may be located along the side of nourishment tube 2, for example at a distance from the tip of nourishment tube 2.

Alternatively or additionally, some or all of light-transmitting fibers 56 and/or light-receiving fibers 58 may be located separately, each in its own sheath.

In embodiments, light-transmitting fiber 56 is replaced by a LED or other light source and electric wires connect to the LED from gastric console 300.

Some substances can be distinguished based on their specific thermal conductivity. The following sensor is one embodiment that uses thermal-based electro-conductivity to determine, for example, the nature of a substance in the digestive tract.

Substance Sensors

Figure 11A:
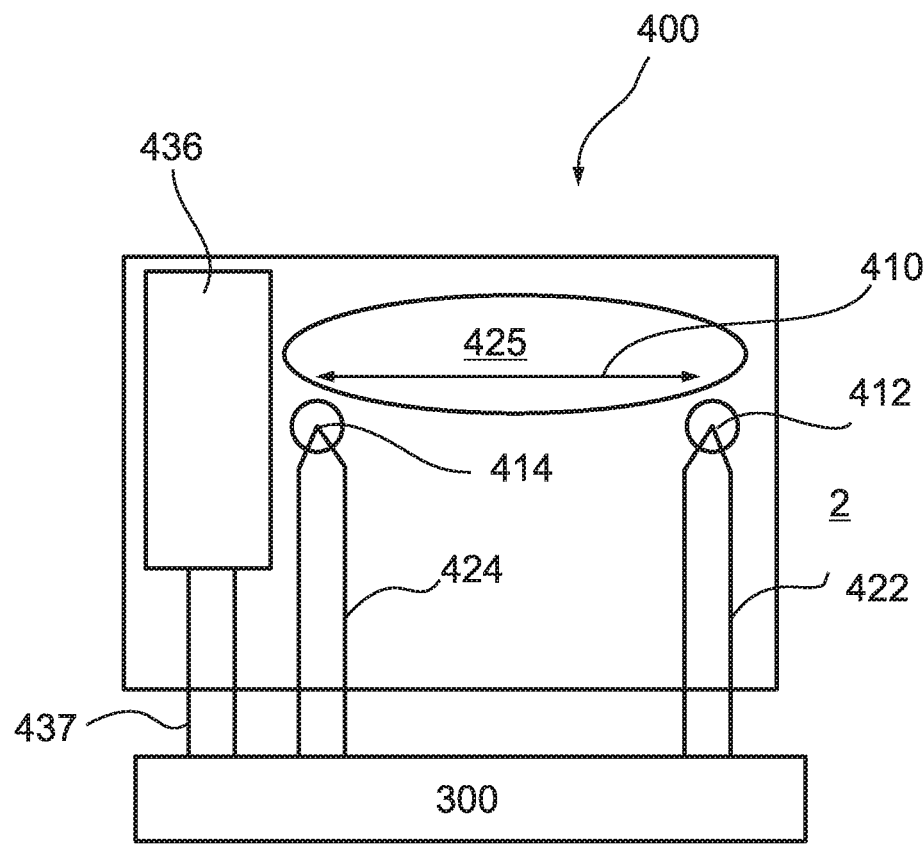
Figure 11B:
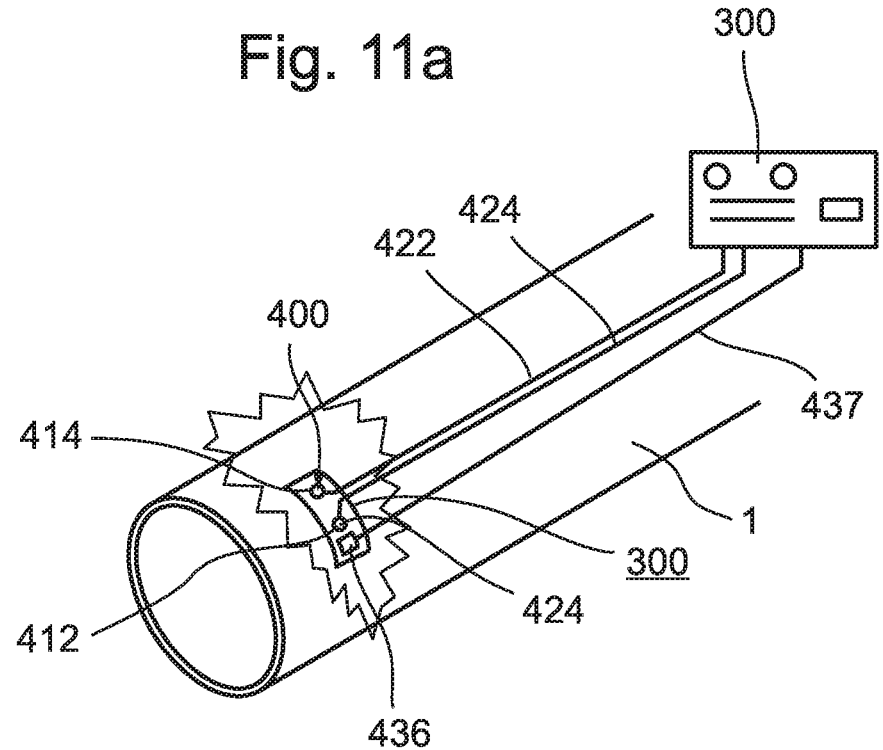

FIGS. 11*a* and 11*b* show a schematic drawing of a substance sensor 400 on suction sleeve 1, which a first temperature sensor 414 is located nearer to a heating element 436 which heats a substance 425 and a second temperature sensor 412 is located farther from heating element 436.

Console 300 compares the temperature of substance 425 as recorded by first temperature sensor 414 and as recorded by second temperature sensor 412, with a distance 410 between sensors 414 and 412 causing the temperature of substance 425 to drop slightly.

Based upon the temperature drop detected from first to and second temperature sensors 414 and 412 respectively, gastric console 300 determines the identity of substance 425 and, in the case of reflux, initiate one of the procedures noted above to spare the end user a case of aspiration.

Alternatively or additionally, the identity of substance 425 can be determined by measuring voltage, current resistance, impedance and/or current conductivity across a distance 410 from which first sensor 414 is separated from a second sensor 412.

Typically, each of sensors 414 and 412 are made from the same metal elements as each other or different from each other.

It is expected that during the life of a patent maturing from this application many relevant interactive NGT system 250 sensor combinations will be developed and the scope of the term NGT sensors is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral fractional or integral within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following theoretical examples, which together with the above descriptions illustrate some embodiments of the invention in a non limiting fashion.

Example 1

A first patient is connected to interactive NGT system 250 and console 300 (FIG. 1*a*). After receiving 100 milliliters of nourishment, the patient produces reflux and console 300 and operator initiates steps to prevent aspiration.

At the next scheduled feeding, console 300 stops nourishment after the patient receives 80 milliliters of nourishment, pauses about 15 minutes to allow digestion and then resumes providing nourishment.

Alternatively, console 300 increases the period of time over which 100 milliliters of nourishment is dispensed, as described above.

Example 2

A second patient who suffers from over-acidification of gastric contents is connected to interactive NGT system 250 and console 300.

Console 300 is programmed with the patient nourishment requirements, including various oral APIs, for example blood thinners and vasodilators and the overall pH level of the stomach that is to be expected when the patient nourishment is dispensed.

Console 300 continually reviews the pH level of the nourishment via a pH sensor located in the stomach. When the pH level lowers below a preset level console 300 automatically administrates a dose of antacid to the stomach, thereby raising the pH level.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

For example, in come embodiments, the controller may be equipped with a motor that pulls the nourishment tube out of the esophagus without manual assistance. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A gastric feeding tube system, comprising:
   a gastric feeding tube having a diameter and length configured to pass through an esophagus;
   at least one sensor positioned on the gastric feeding tube and located to be inside the body of a patient when the gastric feeding tube is in an operative position for feeding the patient;
   a controller adapted for:
   performing an analysis of signals from the at least one sensor, and
   scheduling, according to an outcome of the analysis, feeding of the patient with nourishments via the gastric feeding tube; and
   a calorie counter.

2. The system according to claim 1, wherein the controller is adapted to identify when nourishment is not passing through the gastric feeding tube and generate an alert signal for presentation to an operator.

3. The system according to claim 1, wherein the controller tracks an amount of nourishment provided to the patient via the gastric feeding tube and performs the scheduling accordingly.

4. The system according to claim 1, wherein the controller instructs stopping the feeding of the patient when a reflux is detected based on outputs of the at least one sensor.

5. A gastric feeding tube system, comprising:
   a gastric feeding tube having a diameter and length configured to pass through an esophagus;
   at least one sensor positioned on the gastric feeding tube and located to be inside the body of a patient when the gastric feeding tube is in an operative position for feeding the patient;
   a controller adapted for:
   performing an analysis of signals from the at least one sensor, and
   scheduling, according to an outcome of the analysis, feeding of the patient with nourishments via the gastric feeding tube
   wherein the controller counts calories of nourishment dispensed via the gastric feeding tube and performs the scheduling accordingly.

6. The system according to claim 1, wherein the controller instructs modifying the nourishments according to the outcome of the analysis.

7. The system according to claim 1, wherein the controller changes a feeding rate via the gastric feeding tube according to the outcome of the analysis.

8. The system according to claim 1, wherein the controller activates an electronically controlled fluid switch according to the outcome of the analysis for selecting a source for providing the nourishments.

9. The system according to claim 8, wherein the source are selected from a group consisting of a medicament source, a food source; and a vitamin supplement source.

10. The system according to claim 1, wherein the controller activates a suction source for sucking up gastric fluid via a suction sleeve in the gastric feeding tube according to the outcome of the analysis.

11. The system according to claim 1, wherein the controller performs the scheduling by activating an actuator to control a flow through the gastric feeding tube.

12. The system according to claim 1, wherein the at least one sensor measures electrical resistance and/or impedance in the digestive tract.

13. The system according to claim 1, wherein the controller is programmable to perform the scheduling according to a nourishment plan for the patient.

14. The system according to claim 1, including a nourishment pump operatively associated with the controller and connected to a lumen of the feeding tube, wherein the controller performs the scheduling by controlling the movement of nourishment through the nourishment pump.

15. The system according to claim 1, wherein the controller performs the scheduling according to historic patient information.

16. The system according to claim 1, wherein the controller performs the scheduling according to real time patient information.

17. The system according to claim 1, wherein the controller performs the scheduling according to physiological information.

18. A method of operating a gastric feeding tube system, comprising:
  performing an analysis of signals at least one sensor positioned on a gastric feeding tube having a diameter and length configured to pass through an esophagus when the feeding tube is located inside the body of a patient in an operative position for feeding the patient;
  counting calories of nourishment dispensed via the gastric feeding tube; and
  scheduling, according to an outcome of the analysis and the counted calories, feeding of the patient with nourishments via the gastric feeding tube.

19. A gastric feeding tube system, comprising:
  a gastric feeding tube having a diameter and length configured to pass through an esophagus;
  a calorie counter;
  a controller adapted for:
  performing an analysis of outputs of the calorie counter, and
  scheduling, according to an outcome of the analysis, feeding of the patient with nourishments via the gastric feeding tube.

20. The system according to claim 19, wherein the controller performs the scheduling according to historic patient information.

21. The system according to claim 19, wherein the controller performs the scheduling according to real time patient information.

22. The system according to claim 1, wherein the controller performs the scheduling according to a caloric allotment to the patient.

23. The system according to claim 1, wherein the controller performs the scheduling by instructing an operation of a feeding machine providing the nourishments.

* * * * *